(12) United States Patent
Draghia-Akli et al.

(10) Patent No.: US 7,250,405 B2
(45) Date of Patent: Jul. 31, 2007

(54) MODIFIED PITUITARY GLAND DEVELOPMENT IN OFFSPRING FROM EXPECTANT MOTHER ANIMALS TREATED WITH GROWTH HORMONE RELEASING HORMONE THERAPY

(75) Inventors: Ruxandra Draghia-Akli, Houston, TX (US); Amir Khan, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 497 days.

(21) Appl. No.: 10/359,919

(22) Filed: Feb. 6, 2003

(65) Prior Publication Data
US 2004/0038918 A1 Feb. 26, 2004

Related U.S. Application Data

(60) Provisional application No. 60/355,566, filed on Feb. 7, 2002.

(51) Int. Cl.
A61K 31/70 (2006.01)
C12N 5/00 (2006.01)
C12N 15/00 (2006.01)
C12N 15/63 (2006.01)
C12P 21/06 (2006.01)
A01N 63/00 (2006.01)
A61K 48/00 (2006.01)

(52) U.S. Cl. .................... 514/44; 435/69.1; 435/320.1; 435/325; 435/455; 424/93.1; 424/93.2

(58) Field of Classification Search .................... None
See application file for complete search history.

(56) References Cited

U.S. PATENT DOCUMENTS

| | | |
|---|---|---|
| 4,223,019 A | 9/1980 | Momany |
| 4,223,020 A | 9/1980 | Momany |
| 4,223,021 A | 9/1980 | Momany |
| 4,224,316 A | 9/1980 | Momany |
| 4,226,857 A | 10/1980 | Momany |
| 4,228,156 A | 10/1980 | Momany |
| 4,228,158 A | 10/1980 | Momany |
| 4,410,512 A | 10/1983 | Bowers |
| 4,833,166 A | 5/1989 | Grosvenor |
| 4,839,344 A | 6/1989 | Bowers |
| 5,023,322 A | 6/1991 | Kovacs |
| 5,036,045 A | 7/1991 | Thorner |
| RE33,699 E | 9/1991 | Drengler |
| 5,061,690 A | 10/1991 | Kann |
| 5,084,442 A | 1/1992 | Felix |
| 5,134,120 A | 7/1992 | Boyd |
| 5,137,872 A | 8/1992 | Seely |
| 5,292,721 A | 3/1994 | Boyd |
| 5,486,505 A | 1/1996 | Bowers |
| 5,605,885 A | 2/1997 | Bernton |
| 5,696,089 A | 12/1997 | Felix |
| 5,756,264 A | 5/1998 | Schwartz |
| 5,776,901 A | 7/1998 | Bowers |
| 5,792,747 A | 8/1998 | Schally |
| 5,846,936 A | 12/1998 | Felix |
| 5,847,066 A | 12/1998 | Coy |
| 5,872,127 A | 2/1999 | Cincotta |

FOREIGN PATENT DOCUMENTS

WO       WO 02/061037 A2     8/2002

OTHER PUBLICATIONS

Khan et al. Amer. J. Physiol. 285:E224-E231, 2003.*
Khan et al. Endocrinology 143:3561-3567, 2002.*
Stribey et al Fertility and Sterlity 77:645-657, 2002.*
Goncalves, Bioessays. 27(5):506-517, 2005.*
Juengst, BMJ, 326:1410-11, 2003.*
Rosenberg et al, SCIENCE 287:1751, 2000.*
Anderson, NATURE 392:25-30, 1998.*
Touchette, Nat. Med. 2(1) 7-8, 1996.*
Aihara, H. & Miyazaki, J., Gene transfer into muscle by electroporation in vivo, Nat. Biotechnol. 16, 867-870 (1998).
Albanese, A. and R. Stanhope. 1997. GH treatment induces sustained catch-up growth in children with intrauterine growth retardation: 7-year results. Horm. Res. 48:173-177.
Allen, D.B., A.C. Rundle, D.A. Graves, and S.L. Blethen. 1997. Risk of leukemia in children treated with human growth hormone: review and reanalysis. J.Pediatr. 131:S32-S36.
Aramburo, C., Luna, M., Carranza, M., Reyes, M., Martinez-Coria, H., Scanes, C. G. (2000) Growth hormone size variants: changes in the pituitary during development of the chicken. Proc.Soc.Exp.Biol. Med. 223, 67-74.
Asa, S. L., Kovacs, K., Stefaneanu, L., Horvath, E., Billestrup, N., Gonzalez-Manchon, C., Vale, W. (1992) Pituitary adenomas in mice transgenic for growth hormone-releasing hormone. Endocrinology 131, 2083-2089.
Azcona, C., A. Albanese, P. Bareille, and R. Stanhope. 1998. Growth hormone treatment in growth hormone-sufficient and -insufficient children with intrauterine growth retardation/Russell-Silver syndrome. Horm.Res. 50:22-27.
Barr, E., Leiden, J. M. (1991) Systemic delivery of recombinant proteins by genetically modified myoblasts. Science 254, 1507-1509.
Bartke, A. 1998. Growth hormone and aging. Endocrine 8:103-108.
Benfield, M.R. and E.C. Kohaut. 1997. Growth hormone is safe in children after renal transplantation. J.Pediatr. 131:S28-S31.
Bercu, B.B., R.F. Walker. 1997. Growth hormone secretagogues in children with altered growth. Acta Paediatrica 86:102-106.

(Continued)

Primary Examiner—Sumesh Kaushal
(74) Attorney, Agent, or Firm—Jackson Walker L.L.P.

(57) ABSTRACT

The intramuscular electroporated injection of a protease-resistant growth hormone-releasing hormone ("GHRH") cDNA into rat dams at 16 days of gestation resulted in the enhanced long-term growth of the F1 offspring. The offspring were significantly heavier by one week of age and the difference was sustained to 10 weeks of age. Consistent with their augmented growth, plasma IGF-I concentration of the F1 progeny was increased significantly. The pituitary gland of the offspring was significantly heavier, and contained an increased number of somatotropes (cells producing GH) and lactotrophs (prolactin-secreting cells), and is indicative of an alteration in cell lineages. These unique findings demonstrate that enhanced GHRH expression in pregnant dams can result in intergenerational growth promotion, by altering development of the pituitary gland in the offspring.

16 Claims, 7 Drawing Sheets

OTHER PUBLICATIONS

Bergsma, D.J., Grichnik, J.M., Gossett, L.M. & Schwartz, R.J. Mol. Cell. Biol. 6, 2462-2475 (1986).

Bettan, M., Emmanuel, F., Darteil, R., Caillaud, J. M., Soubrier, F., Delaere, P., Branelec, D., Mahfoudi, A., Duverger, N., Scherman, D. (2000) High-level protein secretion into blood circulation after electric pulse-mediated gene transfer into skeletal muscle. Mol. Ther. 2, 204-210.

Billestrup, N., Gonzalez-Manchon, C., Potter, E., Vale, W. (1990) Inhibition of somatotroph growth and growth hormone biosynthesis by activin in vitro. Mol.Endocrinol. 4, 356-362.

Blethen, S.L. and A.C. Rundle. 1996. Slipped capital femoral epiphysis in children treated with growth hormone. A summary of the National Cooperative Growth Study experience. Horm.Res. 46:113-116.

Borski, R. J., Tsai, W., DeMott-Friberg, R., & Barkan, A. L. (2000) Induction of growth hormone (GH) mRNA by pulsatile GH-releasing hormone in rats is pattern specific. Am.J Physiol Endocrinol. Metab 278, E885-E891.

Bowers, C.Y. 1998. Growth hormone-releasing peptide (GHRP). Cell Mol Life Sci. 54(12):1316-29.

Campbell, R.M., Y. Lee, J. Rivier, E.P. Heimer, A.M. Felix, and T.F. Mowles. 1991. GRF analogs and fragments: correlation between receptor binding, activity and structure. Peptides 12:569-574.

Chung, C. S., Etherton, T. D., Wiggins, J. P. (1985) Stimulation of swine growth by procine growth hormone. J.Anim Sci. 60, 118-130.

Corpas, E., S.M. Harman, and M.R. Blackman. 1993. Human growth hormone and human aging. Endocrine Reviews 14:20-39.

Corpas, E., S.M. Harman, M.A. Pineyro, R. Roberson, and M.R. Blackman. 1993. Continuous subcutaneous infusions of growth hormone (GH) releasing hormone 1-44 for 14 days increase GH and insulin-like growth factor-I levels in old men. Journal of Clinical Endocrinology & Metabolism 76:134-138.

Dahler, A., Wade, R. P., Muscat, G. E., Waters, M. J. (1994) Expression vectors encoding human growth hormone (hGH) controlled by human muscle-specific promoters: prospects for regulated production of hGH delivered by myoblast transfer or intravenous injection. Gene 145, 305-310.

Davis, H.L., Whalen, R.G. & Demeneix, B.A. Hum. Gene Ther. 4, 151-159 (1993).

D'Costa, A.P., R.L. Ingram, J.E. Lenham, and W.E. Sonntag. 1993. The regulation and mechanisms of action of growth hormone and insulin-like growth factor 1 during normal aging. J. Reprod. Fert.-Supp. 46:87-98.

Dhawan, J., Pan, L. C., Pavlath, G. K., Travis, M. A., Lanctot, A. M., Blau, H. M. (1991) Systemic delivery of human growth hormone by injection of genetically engineered myoblasts. Science 254, 1509-1512.

Dieguez C, Casanueva FF. 2000. Ghrelin: a step forward in the understanding of somatotroph cell function and growth regulation. Eur J Endocrinol. 142(5):413-7.

Draghia-Akli, R., Li, X.G., Schwartz, R.J., et al., Enhanced growth by ectopic expression of growth hormone releasing hormone using an injectable myogenic vector, Nat. Biotechnol. 15, 1285-1289 (1997).

Draghia-Akli, et al., Myogenic expression of an injectable protease-resistant growth hormone-releasing hormone augments long-term growth in pigs, Nat Biotechnol, 17(12), 1179-83 (1999).

Dubreuil, P., et al., (1990) Effect of dose and frequency of administration of a potent analog of human growth hormone-releasing factor on hormone secretion and growth in pigs. Journal of Animal Science 68, 1254-1268.

Eicher, E.M. and W.G. Beamer. 1976. Inherited ateliotic dwarfism in mice. Characteristics of the mutation, little, on chromosome 6. J.Hered. 67:87-91.

Esch, F.S., P. Bohlen, et al., 1982. Characterization of a 40 residue peptide from a human pancreatic tumor with growth hormone releasing activity. Biochemical & Biophysical Research communications 109:152-158.

Etherton, T. D., Wiggins, J. P., et al., (1986) Stimulation of pig growth performance by porcine growth hormone and growth hormone-releasing factor. Journal of Animal Science 63, 1389-1399.

Etienne, M., et al., (1992) Effects of administration of growth hormone-releasing factor to sows during late gestation on growth hormone secretion, reproductive traits, and performance of progeny from birth to 100 kilograms live weight. Journal of Animal Science 70, 2212-2220.

Farmer, C., Petitclerc, D., Pelletier, G., Brazeau, P. (1992) Lactation performance of sows injected with growth hormone- releasing factor during gestation and(or) lactation. Journal of Animal Science 70, 2636-2642.

Faglia, G., Arosio, M., Bazzoni, N. (1992) Ectopic acromegaly. [Review]. Endocrinology & Metabolism Clinics of North America 21, 575-595.

Frohman, M.A., T.R. Downs, P. Chomczynski, and L.A. Frohman. 1989. Cloning and characterization of mouse growth hormone-releasing hormone (GRH) complementary DNA: increased GRH messenger RNA levels in the growth hormone-deficient lit/lit mouse. Mol.Endocrinol. 3:1529-1536.

Geffner, M. (1997) Effects of growth hormone and insulin-like growth factor I. Acta Paediatr.Suppl 423, 76-79.

Gesundheit, N. and J.K. Alexander. 1995. Endocrine Therapy with Recombinant Hormones and Growth Factors. In Molecular Endocrinology: Basic Concepts and Clinical Correlations. B.D. Weintraub, editor. Raven Press,Ltd., New York. 491-507.

Gonnella, P. A., Harmatz, P., & Walker, W. A. (1989) Prolactin is transported across the epithelium of the jejunum and ileum of the suckling rat. J Cell Physiol 140, 138-149.

Gonzazalez-Parra, S., Argent, J., et al., (2000) Effect of neonatal and adult testosterone treatment on the cellular composition of the adult female rat anterior pituitary. J. Endocrinol. 164, 265-276.

Gopinath, R., Etherton, T. D. (1989) Effects of porcine growth hormone on glucose metabolism of pigs: I. Acute and chronic effects on plasma glucose and insulin status. J.Anim Sci. 67, 682-688.

Grosvenor, C. E., Picciano, M. F., & Baumrucker, C. R. (1993) Hormones and growth factors in milk. Endocr.Rev. 14, 710-728.

Hataya, Y., Akamizu, T., Takaya, K., Kanamoto, N., Ariyasu, H., Saijo, M., Moriyama, K., Shimatsu, A., Kojima, M., Kangawa, K., Nakao, K. (2001) A low dose of ghrelin stimulates growth hormone (GH) release synergistically with GH-releasing hormone in humans. J Clin.Endocrinol.Metab 86, 4552.

Hattori, N., Saito, T., Yagyu, T., Jiang, B. H., Kitagawa, K., Inagaki, C. (2001) GH, GH receptor, GH secretagogue receptor, and ghrelin expression in human T cells, B cells, and neutrophils. J Clin. Endocrinol.Metab 86, 4284-4291.

Heptulla, R.A., S.D. Boulware, S. Caprio, D. Silver, R.S. Sherwin, and W.V. Tamborlane. 1997. Decreased insulin sensitivity and compensatory hyperinsulinemia after hormone treatment in children with short stature. J.Clin.Endocrinol.Metab. 82:3234-3238.

Horvath, T. L., Diano, S., Sotonyi, P., Heiman, M., Tschop, M. (2001) Minireview: ghrelin and the regulation of energy balance-a hypothalamic perspective. Endocrinology 142, 4163-4169.

Howard, A.D., Feighner, S.D., et al., (1996) Receptor in pituitary and hypothalamus that functions growth hormone release. Science 273: 974-977.

Iranmanesh, A., G. Lizarralde, and J.D. Veldhuis. 1991. Age and relative adiposity are specific negative determinants of the frequency and amplitude of growth hormone (GH) secretory bursts and the half-life of endogenous GH in healthy men. Journal of Clinical Endocrinology & Metabolism 73:1081-1088.

Jacobs, P.A., P.R. Betts, A.E. Cockwell, J.A. Crolla, M.J. Mackenzie, D.O. Robinson, and S.A. Youings. 1990. A cytogenetic and molecular reappraisal of a series of patients with Turner's syndrome. Ann.Hum.Genet. 54:209-223.

Jaffe, H.A., C. Danel, G. Longenecker, M. Metzger, Y. Setoguchi, M.A. Rosenfeld, T.W. Gant, S.S. Thorgeirsson, L.D. Stratford-Perricaudet, M. Perricaudet, A. Pavirani, J.-P. Lecocq and R.G. Crystal. 1992. Adenovirus?mediated in vivo gene transfer and expression in normal rat liver. Nat Genet 1(5):372?8.

Kamegai, J. et al. (2001) Regulation of the ghrelin gene: growth hormone-releasing hormone upregulates ghrelin mRNA in the pituitary. Endocrinology 142, 4154-4157.

Key, L.L.J. and A.J. Gross. 1996. Response to growth hormone in children with chondrodysplasia. J.Pediatr. 128:S14-S17.

Klindt, J., Yen, J. T., Buonomo, F. C., Roberts, A. J., Wise, T. (1998) Growth, body composition, and endocrine responses to chronic administration of insulin-like growth factor I and(or) porcine growth hormone in pigs. J.Anim Sci. 76, 2368-2381.

Koch, Y., Werner, H., & Fridkin, M. (1991) Hypothalamic hormones in milk. Endocr.Regul. 25, 128-133.

Li, X., Eastman, E. M., Schwartz, R. J., & Draghia-Akli, Synthetic muscle promoters: activities exceeding naturally occurring regulatory sequences, Nat. Biotechnol. 17. 3, 241-245 (1999).

Lopez-Calderon, A., Soto, L., Villanua, M. A., Vidarte, L., Martin, A. I. (1999) The effect of cyclosporine administration on growth hormone release and serum concentrations of insulin-like growth factor-I in male rats. Life Sci. 64, 1473-1483.

Melmed, S. (1991) Extrapituitary Acromegaly. [Review]. Endocrinology & Metabolism Clinics of North America 20, 507-518.

Miller, K. F., Bolt, D. J., Pursel, V. G., Hammer, R. E., Pinkert, C. A., Palmiter, R. D., Brinster, R. L. (1989) Expression of human or bovine growth hormone gene with a mouse metallothionein-1 promoter in transgenic swine alters the secretion of porcine growth hormone and insulin-like growth factor-I. J.Endocrinol. 120, 481-488.

Mir, L. M., Bureau, M. F., Gehl, J., Rangara, R., Rouy, D., Caillaud, J. M., Delaere, P., Branellec, D., Schwartz, B., Scherman, D. (1999) High-efficiency gene transfer into skeletal muscle mediated by electric pulses. Proc.Natl.Acad.Sci.U.S.A 96, 4262-4267.

Morel, G., Gallego, R., Boulanger, L., Pintos, E., Garcia-Caballero, T., Gaudreau, P. (1999) Restricted presence of the growth hormone-releasing hormone receptor to somatotropes in rat and human pituitaries. Neuroendocrinology 70, 128-136.

Muramatsu, T., Nakamura, A. & Park, H.M., In vivo electroporation: A powerful and convenient means of nonviral gene transfer to tissues of living animals (Review), Int.J.Mol.Med. 1, 55-62 (1998).

Murray, R. A., Maheshwari, H. G., Russell, E. J., Baumann, G. (2000) Pituitary hypoplasia in patients with a mutation in the growth hormone-releasing hormone receptor gene. AJNR Am.J Neuroradiol. 21, 685-689.

Pong, S.-S., Chaung, L.-Y. P., Dean, D.C., Nargund, R.P., Patchett, A.A. and Smith, R.G. (1996). Identification of new G-protein-linked receptor for growth hormone secretagogues. Molecular Endocrinology 10: 57-61.

Pursel, V. G., Hammer, R. E., Bolt, D. J., Palmiter, R. D., Brinster, R. L. (1990) Integration, expression and germ-line transmission of growth- related genes in pigs. [Review] [33 refs]. Journal of Reproduction & Fertility—Supplement 41, 77-87.

Rawlings, S. R., Piuz, I., Schlegel, W., Bockaert, J., Journot, L. (1995) Differential expression of pituitary adenylate cyclase-activating polypeptide/vasoactive intestinal polypeptide receptor subtypes in clonal pituitary somatotrophs and gonadotrophs. Endocrinology 136, 2088-2098.

Rosenfeld, M.A., K Yoshimura, L.E. Stier, B.C. Trapnell, L.D. Stratford-Perricaudet, M. Perricaudet, W. Dalemans, S. Jallat, A. Mercenier, A. Pavirani, J.P. Lecocq, W.B. Guggino, R.G. Crystal. 1991. In vivo transfer of the human cystic fibrosis gene to the respiratory epithelium. Clinical Research 39 (2), 311A.

Rosenfeld, M.A., W Siegfried, K Yoshimura, K Yoneyama, M Fukayama, LE Stier, PK Paakko, P Gilardi, LD Stratford?Perricaudet, M Perricaudet, S. Jallat, A. Pavirani, J.-P. Lecocq, and R.G. Crystal. 1991. Adenovirus?mediated transfer of a recombinant alpha 1?antitrypsin gene to the lung epithelium in vivo. Science 252(5004):431?4.

Sano, T., Asa, S. L., Kovacs, K. (1988) Growth hormone-releasing hormone-producing tumors: clinical, biochemical, and morphological manifestations. Endocr.Rev. 9, 357-373.

Scanlon, M.F., B.G. Issa, and C. Dieguez. 1996. Regulation of Growth Hormone Secretion. Hormone Research 46:149-154.

Shalet, S.M., B.M. Brennan, and R.E. Reddingius. 1997. Growth hormone therapy and malignancy. Horm.Res. 48 Suppl 4:29-32:29-32.

Skuse, D.H., K. Elgar, and E. Morris. 1999. Quality of life in Turner syndrome is related to chromosomal constitution: implication for genetic counseling and management. Acta Paediatrica Scandin. —Supp. 428:110-113.

Smith, V. G., Leman, A. D., Seaman, W. J., VanRavenswaay, F. (1991) Pig weaning weight and changes in hematology and blood chemistry of sows injected with recombinant porcine somatotropin during lactation. J.Anim Sci. 69, 3501-3510.

Smith, R.G., Van der Ploeg, L.H.T., Cheng, K., Hickey, G.J., Wyvratt, Jr., M.J., Fisher, M.H., Nargund, R.P., Patchett, A.A. (1997) Peptidomimetic regulation of growth hormone (GH)secretion. Endocrine Reviews 18: 621-645.

Sohmiya, M., K. Ishikawa, and Y. Kato. 1998. Stimulation of erythropoietin secretion by continuous subcutaneous infusion of recombinant human GH in anemic patients with chronic renal failure. Eur.J.Endocrinol. 138:302-306.

Su, C.M., L.R. Jensen, E.P. Heimer, A.M. Felix, Y.C. Pan, and T.F. Mowles. 1991. In vitro stability of growth hormone releasing factor (GRF) analogs in porcine plasma. Hormone & Metabolic Research 23:15-21.

Szabo, M. & Cuttler, L. (1986) Differential responsiveness of the somatotroph to growth hormone-releasing factor during early neonatal development in the rat. Endocrinology 118, 69-73.

Tamaki, T. & Uchiyama, S. (1995) Absolute and relative growth of rat skeletal muscle. Physiol Behav. 57, 913-919.

Tanaka, H., T. Kubo, T. Yamate, T. Ono, S. Kanzaki, and Y. Seino. 1998. Effect of growth hormone therapy in children with achondroplasia: growth pattern, hypothalamic-pituitary function, and genotype. Eur.J.Endocrinol. 138:275-280.

Tanner, J.W., Davis, S.K., McArthur, N.H., French, J.T. & Welsh, T.H., Jr.m Modulation of growth hormone (GH) secretion and GH mRNA levels by GH-releasing factor, somatostatin and secretagogues in cultured bovine adenohypophysial cells, J.Endocrinol. 125, 109-115 (1990).

Thorner, M. O., Hartman, M. L., Vance, M. L., Pezzoli, S. S., Ampleford, E. J. (1995) Neuroendocrine regulation of growth hormone secretion. [Review]. Neuroscience & Biobehavioral Reviews 19, 465-468.

Thorner, M.O., L.A. Frohman, D.A. Leong, J. Thominet, T. Downs, P. Hellmann, J. Chitwood, J.M. Vaughan, and W. Vale. 1984. Extrahypothalamic growth-hormone-releasing factor (GRF) secretion is a rare cause of acromegaly: plasma GRF levels in 177 acromegalic patients. Journal of Clinical Endocrinology & Metabolism 59:846-849.

Tipton, K. D. (2001) Gender differences in protein metabolism. Curr.Opin.Clin.Nutr.Metab Care 4, 493-498.

Tomic, M., Zivadinovic, D., Van Goor, F., Yuan, D., Koshimizu, T., Stojilkovic, S. S. (1999) Expression of Ca(2+)-mobilizing endothelin(A) receptors and their role in the control of Ca(2+) influx and growth hormone secretion in pituitary somatotrophs. J Neurosci. 19, 7721-7731.

Tripathy, S.K., Svensson, E.C., Black, H.B., et al. Proc.Natl.Acad. Sci.USA 93, 10876-10880 (1996).

Veldhuis, J. D. (1998) Neuroendocrine control of pulsatile growth hormone release in the human: relationship with gender. Growth Horm.IGF.Res. 8 Suppl B, 49-59.

Walter, R., W.H. Simmons, and T. Yoshimoto. 1980. Proline specific endo- and exopeptidases. Mol.Cell Biochem. 30:111-127.

Watkins, S.L. 1996. Bone disease in patients receiving growth hormone. Kidney Int.Suppl. 53:S126-7:S126-S127.

Wolff, J. A., Ludtke, J. J., Acsadi, G., Williams, P., Jani, A. (1992) Long-term persistence of plasmid DNA and foreign gene expression in mouse muscle. Human Molecular Genetics 1, 363-369.

Chen D. Biotechnologies for Improving Animal Metabolism and Growth: A Review. Asian-Australasian Journal of Animal Sciences. Dec. 2001;14(12):1794-1802.

Khan AS, Fiorotto ML, Hill LA, Malone PB, Cummings K, Parghi D, Schwartz RJ, Smith RG, Draghia-Akli R. GHRH Gene Delivery to Pregnant Rats Increases Somatotroph Polulation and Growth of Pups. Soc. for Neuroscience Abstract Viewer and Itinerary Planner. 2002;2002:74.3.

Khan AS, Fiorotto ML, Hill LA, Malone PB, Cummings KK, Parghi D, Schwartz RJ, Smith RG, Draghia-Akli R. Nonhereditary enhancement of progeny growth. Endocrinology. Sep. 2002;143(9):3561-7.

Supplementary Partial European Search Report Under Article 157(2)(a) EPC from the European Patent Office dated Mar. 14, 2006.

* cited by examiner

MODIFIED PITUITARY GLAND DEVELOPMENT IN OFFSPRING FROM EXPECTANT MOTHER ANIMALS TREATED WITH GROWTH HORMONE RELEASING HORMONE THERAPY

RELATED APPLICATIONS

This application claims priority to U.S. Provisional Patent Application, Ser. No. 60/355,566, entitled "MODIFIED PITUITARY GLAND DEVELOPMENT IN OFFSPRING FROM EXPECTANT MOTHER ANIMALS TREATED WITH GROWTH HORMONE RELEASING HORMONE THERAPY," filed on Feb. 07, 2002, the entire content of which is hereby incorporated by reference.

BACKGROUND

The present invention pertains to a plasmid-meditated gene supplementation to alter pituitary development, and to increase prolactin levels, in an offspring of a female subject. More specifically, the present invention pertains to administering to a female subject a nucleic acid expression construct that encodes growth hormone releasing hormone ("GHRH") to alter the pituitary development and pituitary hormone secretion (e.g. prolactin) in the offspring from the female subject.

The pituitary gland is an important link between the nervous system and the endocrine system. The pituitary gland is known to release many hormones that affect growth, sexual development, metabolism (e.g. protein, lipid and carbohydrate), glucocorticoids and the reproductive system. The pituitary gland has also been shown to release hormones that affect bone growth and regulate activity in other hormone secreting glands. This invention relates a method for altering pituitary gland development in offspring from female subjects that have been treated with a nucleic acid construct that encodes a growth hormone releasing hormone ("GHRH") or functional biological equivalent. The expression of the GHRH or biological equivalent thereof is regulated by a tissue specific promoter (e.g. a myogenic promoter). When female subjects are treated with the nucleic acid construct that encodes GHRH, many physiological changes occur in the female subject directly. However, when female subjects are treated with the GHRH construct prior to, or during a gestation period, the offspring from these treated female subjects undergo similar physiological changes. For example, the subsequent expression and ensuing release of GHRH or biological equivalent thereof by the modified cells in the female subject results in the altered development of the pituitary gland in their offspring. Additionally, hormones secreted by the pituitary gland are increased in offspring from treated female subjects when compared to the offspring from control treated female subjects. More specifically, the pituitary gland is increased in sized and the levels of the multifunctional hormone prolactin is elevated utilizing this method.

The pituitary gland has two distinct parts, the anterior and the posterior lobes, each of which releases different hormones. The pituitary gland appears to be subservient in part to the hypothalamus. Pituitary gland development, including regulation and differentiation of somatotrophs, depends upon paracrine processes within the pituitary itself and involves several growth factors and neuropeptides. Secretion of growth hormone ("GH") is stimulated by the natural GH secretagogue, called growth hormone releasing hormone ("GHRH"), and inhibited by somatostatin ("SS"). The central role of growth hormone ("GH") is controlling somatic growth in humans and other vertebrates, and the physiologically relevant pathways that regulate GH secretion from the pituitary are well known. For example, the GH production pathway is composed of a series of interdependent genes whose products are required for normal growth. The GH pathway genes include: (1) ligands, such as GH and insulin-like growth factor-I ("IGF-I"); (2) transcription factors such as prophet of pit 1, or prop 1, and pit 1: (3) stimulatory and inhibitory factors, such as growth hormone releasing hormone ("GHRH") and somatostatin ("SS"), respectively; and (4) receptors, such as GHRH receptor ("GHRH-R") and the GH receptor ("GH-R"). These genes are expressed in different organs and tissues, including but not limited to the hypothalamus, pituitary, liver, and bone. Effective and regulated expression of the GH pathway is essential for optimal linear growth, as well as homeostasis of carbohydrate, protein, and fat metabolism. GH synthesis and secretion from the anterior pituitary is stimulated by GHRH and inhibited by somatostatin, which are both hypothalamic hormones. GH stimulates production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

The immune function is modulated by IGF-I, which has two major effects on B cell development: potentiation and maturation, and as a B-cell proliferation cofactor that works together with interlukin-7 ("IL-7"). These activities were identified through the use of anti-IGF-I antibodies, antisense sequences to IGF-I, and the use of recombinant IGF-I to substitute for the activity. There is evidence that macrophages are a rich source of IGF-I. The treatment of mice with recombinant IGF-I confirmed these observations as it increased the number of pre-B and mature B cells in bone marrow. The mature B cell remained sensitive to IGF-I as immunoglobulin production was also stimulated by IGF-I in vitro and in vivo.

The production of recombinant proteins in the last 2 decades provided a useful tool for the treatment of many diverse conditions. For example, recombinant GH administration has been used to treat GH-deficiencies in short stature children, or as an anabolic agent in burn, sepsis, and as well as in the elderly and AIDS patients. However, resistance to GH action has been reported in malnutrition and infection. Long-term studies on transgenic animals and in patients undergoing GH therapies have shown no causal correlation between GH or IGF-I therapy and cancer development. GH replacement therapy is widely used clinically, with beneficial effects, but therapy is associated several disadvantages: GH must be administered subcutaneously or intramuscularly once a day to three times a week for months, or usually years; insulin resistance and impaired glucose tolerance can occur; accelerated bone epiphysis growth and closure has been observed in pediatric patients (*Blethen*, S. L., et al. 1996).

In contrast, essentially no side effects have been reported for recombinant GHRH therapies. Extracranially secreted GHRH, as mature peptide or truncated molecules (as seen with pancreatic islet cell tumors and variously located carcinoids) are often biologically active and can even produce acromegaly (*Esch*, et al., 1982; *Thorner*, et al., 1984). Administration of recombinant GHRH to GH-deficient children or adult humans augments IGF-I levels, increases GH secretion proportionally to the GHRH dose, yet still invokes a response to bolus doses of recombinant GHRH (*Bercu and*

*Walker*, 1997). Thus, GHRH administration represents a more physiological alternative of increasing subnormal GH and IGF-I levels (*Corpas*, et al., 1993).

GH is released in a distinctive pulsatile pattern that has profound importance for its biological activity (*Argente*, et al., 1996). Secretion of GH is stimulated by the GHRH, and inhibited by somatostatin, and both are hypothalamic hormones (*Thorner*, et al., 1995). GH pulses are a result of GHRH secretion that is associated with a diminution or withdrawal of somatostatin secretion. In addition, the pulse generator mechanism is timed by GH-negative feedback. The endogenous rhythm of GH secretion becomes entrained to the imposed rhythm of exogenous GH administration. Effective and regulated expression of the GH and insulin-like growth factor-I ("IGF-I") pathway is essential for optimal linear growth, homeostasis of carbohydrate, protein, and fat metabolism, and for providing a positive nitrogen balance (*Murray*, et al., 2000). Numerous studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies (*Dubreuil*, et al., 1990). Although recombinant GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, recombinant GHRH administration is not practical.

Wild type GHRH has a relatively short half-life in the circulatory system, both in humans (*Frohman*, et al., 1984) and in farm animals. After 60 minutes of incubation in plasma, 95% of the GHRH(1-44)NH2 is degraded, while incubation of the shorter (1-40)OH form of the hormone, under similar conditions, shows only a 77% degradation of the peptide after 60 minutes of incubation (*Frohman*, et al., 1989). Incorporation of cDNA coding for a particular protease-resistant GHRH analog in a gene transfer vector results in a molecule with a longer half-life in serum, increased potency, and provides greater GH release in plasmid-injected animals (*Draghia-Akli*, et al., 1999, herein incorporated by reference). Mutagenesis via amino acid replacement of protease sensitive amino acids prolongs the serum half-life of the GHRH molecule. Furthermore, the enhancement of biological activity of GHRH is achieved by using super-active analogs that may increase its binding affinity to specific receptors (*Draghia-Akli*, et al, 1999).

Extracranially secreted GHRH, as processed protein species GHRH(1-40) hydroxy or GHRH(1-44) amide or even as shorter truncated molecules, are biological active (*Thorner*, et al., 1984). It has been reported that a low level of GHRH (100 pg/ml) in the blood supply stimulates GH secretion (*Corpas*, et al., 1993). Direct plasmid DNA gene transfer is currently the basis of many emerging gene therapy strategies and thus does not require viral genes or lipid particles (*Muramatsu*, et al., 1998; *Aihara and Miyazaki*, 1998). Skeletal muscle is target tissue, because muscle fiber has a long life span and can be transduced by circular DNA plasmids that express over months or years in an immunocompetent host (*Davis*, et al., 1993; *Tripathy*, et al., 1996). Previous reports demonstrated that human GHRH cDNA could be delivered to muscle by an injectable myogenic expression vector in mice where it transiently stimulated GH secretion to a modes extent over a period of two weeks (*Draghia-Akli*, et al., 1997).

Administering novel GHRH analog proteins (U.S. Pat. Nos. 5,847,066; 5,846,936; 5,792,747; 5,776,901; 5,696,089; 5,486,505; 5,137,872; 5,084,442, 5,036,045; 5,023,322; 4,839,344; 4,410,512, RE33,699) or synthetic or naturally occurring peptide fragments of GHRH (U.S. Pat. Nos. 4,833,166; 4,228,158; 4,228,156; 4,226,857; 4,224,316; 4,223,021; 4,223,020; 4,223, 019) for the purpose of increasing release of growth hormone have been reported. A GHRH analog containing the following mutations have been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. patent application Ser. No. 09/624,268 ("the '268 application"), which teaches application of a GHRH analog containing mutations that improve the ability to elicit the release of growth hormone. In addition, the '268 application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference.

U.S. Pat. No. 5,061,690 is directed toward increasing both birth weight and milk production by supplying to pregnant female mammals an effective amount of human GHRH or one of it analogs for 10-20 days. Application of the analogs lasts only throughout the lactation period. However, multiple administrations are needed. A co-pending disclosure regarding administration of the growth hormone releasing hormone (or factor) as a DNA molecule, such as with plasmid mediated therapy techniques has been disclosed (U.S. patent application Ser. No. 10/021,403).

U.S. Pat. No. 5,134,120 ("the '120 patent") and U.S. Pat. No. 5,292,721 ("the '721 patent") teach that by deliberately increasing growth hormone in swine during the last 2 weeks of pregnancy through a 3 week lactation resulted in the newborn piglets having marked enhancement of the ability to maintain plasma concentrations of glucose and free fatty acids when fasted after birth. In addition, the '120 and '721 patents teach that treatment of the sow during lactation results in increased milk fat in the colostrum and an increased milk yield. These effects are important in enhancing survivability of newborn pigs and weight gain prior to weaning. However, the '120 and '721 patents provide no teachings regarding administration of the growth hormone releasing hormone ("GHRH") as a DNA form.

Prolactin is a single-chain protein hormone closely related to growth hormone. It is chiefly secreted by lactotrophs in the anterior pituitary. However, prolactin is also synthesized and secreted by a broad range of other cells in the body, most prominently various immune cells, the brain and the decidua of the pregnant uterus. Prolactin is also found in the serum of normal females and males. Prolactin secretion is pulsatile and also shows diurnal variation, with the serum concentration increasing during sleep and the lowest level occurs about 3 hours after waking. The secretion of prolactin is increased by stress and appears to be dependent upon a women's estrogen status.

The conventional view of prolactin is that the mammary gland is its major target organ, and stimulating mammary gland development along with milk production define its major functions. Although these views are true, such descriptions fail to convey an accurate depiction of this multifunctional hormone. For example, it is difficult to find a mammalian tissue that does not express prolactin receptors, and although the anterior pituitary is the major source of prolactin, the hormone is synthesized and secreted in many other tissues. Overall, several hundred different actions have been reported for prolactin in various species. Some of prolactin's major effects are summarized below.

Prolactin's major known functions are attributed with mammary gland development, milk production and reproduction. In the 1920's it was found that extracts of the pituitary gland, when injected into virgin rabbits, induced milk production. Subsequent research demonstrated that prolactin has two major roles in milk production:

Prolactin induces lobulo-alveolar growth of the mammary gland, wherein the alveoli are the clusters of cells in the mammary gland that actually secrete milk.

Prolactin stimulates lactogenesis or milk production after giving birth. Prolactin, along with cortisol and insulin, act together to stimulate transcription of the genes that encode milk proteins. The critical role of prolactin in lactation has been established by utilizing transgenic mice with targeted deletions in the prolactin gene. Female mice that are heterozygous for the deleted prolactin gene only produce about half the normal amount of prolactin, and fail to lactate after their first pregnancy.

Prolactin is also important in several non-lactational aspects of reproduction. For example, in some species (e.g. rodents, dogs, skunks), prolactin is necessary for maintenance of ovarian structures (i.e. corpora lutea) that secrete progesterone. Mice that are homozygous for an inactivated prolactin gene and thus incapable of secreting prolactin are infertile due to defects in ovulation, fertilization, preimplantation development and implantation. Prolactin also appears to have stimulatory effects in some species on reproductive or maternal behaviors such as nest building and retrieval of scattered young.

Prolactin also appears to elicit effects in the immune system. For example, the prolactin receptor is widely expressed by immune cells, and some types of lymphocytes synthesize and secrete prolactin. These observations suggest that prolactin may act as an autocrine or paracrine modulator of immune activity. Conversely, mice with homozygous deletions of the prolactin gene fail to show significant abnormalities in immune responses. A considerable amount of research is in progress to delineate the role of prolactin in normal and pathologic immune responses. However, the significance of these potential functions remains poorly understood.

Administering prolactin stimulating hormones, or prolactin agonists (U.S. Pat. Nos. 5,605,885; and 5,872,127) for the purpose of stimulating the immune system have been reported. The U.S. Pat. No. 5,872,127 ("the '127 patent") filed by Cincotta in 1999 discloses methods for treating a disorder of the immune system or an immunodeficiency state that comprise the steps of administering to a patient an effective amount a serotonin agonist and at a dopamine agonist, where the combination of the serotonin agonist and the dopamine agonist are present in an amount effective to treat a patient's immuno-compromised condition. The administration of each of the agents is confined to a specific time of day that is capable of adjusting the prolactin profile of the patient to conform or to approach the standard human prolactin profile.

Additionally, the supplementation of the prolactin agonists in U.S. Pat. No. 5,605,885 ("the '885 patent") disclose a method for the stimulation of a suppressed or deficient immune system by regulating the blood levels or activity of the hormone prolactin directly. The '885 patent method comprises treating an immunosuppressed subject with proteins, peptides and compounds that have prolactin-like activity including, but not limited to, prolactin, peptide sequences from prolactin that have prolactin-like activity, growth hormone (a structurally similar and biologically related hormone), or peptide sequences from growth hormone which have prolactin-like activity, placental lactogens, and any genetically engineered protein sequence which has prolactin-like activity. However, neither the '885 and '127 patents provide teachings regarding increasing prolactin levels by the administration of the growth hormone releasing hormone ("GHRH") as a DNA form.

In summary, the production of recombinant proteins in the last 2 decades provides a useful tool for the treatment of many diverse conditions, however these treatments have some significant drawbacks. It has also been demonstrated that nucleic acid expression constructs that encode recombinant proteins are viable solutions to the problems of frequent injections and high cost of traditional recombinant therapy. By utilizing knowledge of specific pituitary/hypothalamic pathways and the functionality of extracranially secreted hormones, it is possible to treat many conditions utilizing a plasmid-mediated introduction of a nucleic acid construct into a subject. Furthermore, it has been shown that some beneficial effects can be conferred to the offspring of female subjects that have been treated utilizing recombinant proteins during gestation and without treating the offspring directly. Thus, this invention is related to the conferred beneficial effects in offspring from GHRH treated mothers. More specifically this invention discloses methods for altering pituitary development and pituitary hormone secretion (e.g. prolactin) in the offspring from female subjects treated with nucleic acid constructs that encode GHRH.

SUMMARY

The present invention pertains to a plasmid-meditated gene supplementation to alter pituitary development, and to increase prolactin levels, in an offspring of a female subject. One embodiment of the present invention pertains to administering to a female subject a nucleic acid expression construct that encodes growth hormone releasing hormone ("GHRH") to alter the pituitary development and pituitary hormone secretion (e.g. prolactin, "PRL") in the offspring from the female subject.

The present plasmid-mediated gene supplementation method results in an increase in the pituitary lactotrophs (pituitary cells that specifically produce prolactin), an increase in the number and production of PRL by the pituitary gland, and an increase in the prolactin levels in an offspring from the female subject.

The female subject may be a mother, a female who has never been pregnant or given birth before, or a surrogate mother, such as impregnated by fetal transplantation. Although the nucleic acid construct can be in a variety of different configurations, a preferred embodiment of the construct comprises a promoter, a nucleotide sequence, and a 3' untranslated region. The nucleic acid sequence may comprise a growth hormone releasing hormone ("GHRH") or a biological equivalent thereof, a myogenic promoter, and a specified 3' untranslated region. Another embodiment includes the use of modified GHRH analogs that have been engineered to be protease resistant, but retain the functional biological activity of the wild-type GHRH. The delivery of the nucleic acid expression construct into the female subject may be accompanied or assisted. Although electroporation is a preferred method to deliver the nucleic acid expression construct into the cells of the female subject, other approaches can be utilized for this purpose. In a specific embodiment of the current invention, muscle cells are the preferred cell type for delivery of the nucleic acid expression construct, however, other cell types (e.g. somatic cells, stem cells, or germ cells) can be utilized.

DETAILED DESCRIPTION OF THE PREFERRED EMBODIMENTS

Terms

Figure 1:
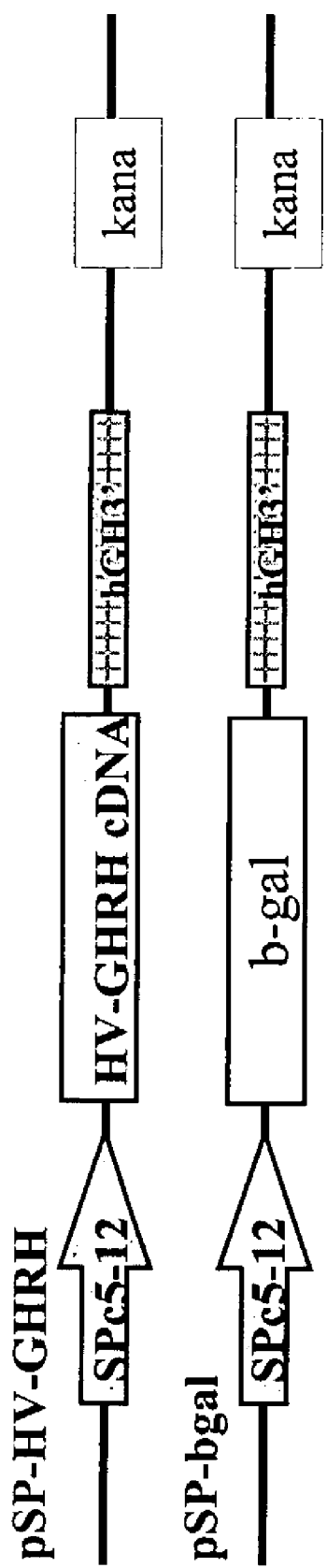
FIG. 1 shows the nucleic acid constructs that were used in pregnant rats. Thirty micrograms of a pSP-HV-GHRH (SEQID#11) nucleic acid construct was delivered into the tibialis anterior muscle of rat dams at 16 days of gestation. Control dams were injected with a similar construct driving the reporter, beta-galactosidase. The injection was followed by in vivo electroporation.

It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "animal" as used herein refers to any species of the animal kingdom. In preferred embodiments it refers more specifically to humans, animals in their wild state, animals used as pets (birds, dogs, cats, horses), animals used for work (horses, cows, dogs) and animals which produce food (chickens, cows, fish), farm animals (pigs, horses, cows, sheep, chickens) or are themselves food (frogs, chickens, fish, crabs, lobsters, shrimp, mussels, scallops, goats, boars, cows, lambs, pigs, ostrich, emu, eel) and other animals well known to the art.

The term "effective amount" as used herein is defined as the amount of the composition required to produce an effect in a host which can be monitored using several endpoints known to those skilled in the art. In a specific embodiment, these endpoints are surrogate markers.

The term "feed conversion efficiency" as used herein is defined as the amount of food an animal eats per day versus the amount of weight gained by said animal. The terms "efficiency" or "feed efficiency" as used herein is interchangeable with "feed conversion efficiency."

The term "growth deficiencies" as used herein is defined as any health status, medical condition or disease in which growth is less than normal. The deficiency could be the result of an aberration directly affecting a growth hormone pathway (such as the GHRH-GH-IGF-I axis), indirectly affecting a growth hormone pathway, or not affecting a growth hormone pathway at all.

The term "growth hormone" as used herein is defined as a hormone which relates to growth and acts as a chemical messenger to exert its action on a target cell.

The term "growth hormone releasing hormone" as used herein is defined as a hormone which facilitates or stimulates release of growth hormone.

The term "growth hormone releasing hormone analog" as used herein is defined as a protein which contains amino acid mutations and/or deletions in the naturally occurring form of the amino acid sequence (with no synthetic dextro or cyclic amino acids), but not naturally occurring in the GHRH molecule, yet still retains its function to enhance synthesis and secretion of growth hormone.

The term "growth hormone secretagogue receptor" (GHS-R) as used herein is defined as a receptor for a small synthetic compound which is associated, either directly or indirectly, with release of growth hormone from the pituitary gland.

The term "ligand for a growth hormone secretagogue receptor" as used herein is defined as any compound which acts as an agonist on a growth hormone secretagogue receptor. The ligand may be synthetic or naturally occurring. The ligand may be a peptide, protein, sugar, carbohydrate, lipid, nucleic acid or a combination thereof.

The term "myogenic" as used herein refers specifically to muscle tissue.

The term "newborn" as used herein refers to an animal immediately after birth and all subsequent stages of maturity or growth.

The term "offspring" as used herein refers to a progeny of a parent, wherein the progeny is an unborn fetus or a newborn.

The term "parenteral" as used herein refers to a mechanism for introduction of material into an animal other than through the intestinal canal. In specific embodiments, parenteral includes subcutaneous, intramuscular, intravenous, intrathecal, intraperitoneal, or others.

The term "pharmaceutically acceptable" as used herein refers to a compound wherein administration of said compound can be tolerated by a recipient mammal.

The term "secretagogue" as used herein refers to a natural synthetic molecule that enhances synthesis and secretion of a downstream—regulated molecule (e.g. GHRH is a secretagogue for GH).

The term "somatotroph" as used herein refers to a cell which produces growth hormone.

The term "lactotroph" as used herein refers to a cell which produces prolactin.

The term "therapeutically effective amount" as used herein refers to the amount of a compound administered wherein said amount is physiologically significant. An agent is physiologically significant if its presence results in technical change in the physiology of a recipient animal. For example, in the treatment of growth deficiencies, a composition which increases growth would be therapeutically effective; in consumption diseases a composition which would decrease the rate of loss or increase the growth would be therapeutically effective.

The term "vector" as used herein refers to any vehicle which delivers a nucleic acid into a cell or organism. Examples include plasmids, viral vectors, liposomes, or cationic lipids. In a specific embodiment, liposomes and cationic lipids are adjuvant (carriers) that can be complexed with other vectors to increase the uptake of plasmid or viral vectors by a target cell. In a preferred embodiment, the vector comprises a promoter, a nucleotide sequence, preferably encoding a growth hormone releasing hormone, its biological equivalent, or its analog, and a 3' untranslated region. In another preferred embodiment, the promoter, nucleotide sequence, and 3' untranslated region are linked operably for expression in a eukaryotic cell.

The term "nucleic acid expression construct" as used herein refers to any type of genetic construct comprising a nucleic acid coding for a RNA capable of being transcribed. The term "expression vector" can also be used interchangeably.

The term "functional biological equivalent" of GHRH as used herein is a polypeptide that has been engineered to contain a distinct amino acid sequence while simultaneously having similar or improved biologically activity when compared to the GHRH polypeptide.

The term "functional nucleic acid equivalent" of a referenced nucleic acid sequence as used herein means a nucleic acid sequences that has been engineered to contain a distinct nucleic acid sequences while simultaneously having similar or improved functional activity when compared to the referenced nucleic acid sequence. For example, because the universal code is redundant, different codon sequences can express the same amino acid (e.g. ACC, ACA and ACG all code for threonine). Thus, a codon in an expression construct can be changed or optimized, but still codes for an identical amino acid. Similarly, entire functional nucleic acid sequences in an expression vector can be added or deleted without changing the overall functionality of the expression vector. For example, antibiotic resistant genes that are used as selection markers for expression construct replication in bacteria can be added, deleted, or interchanged without altering the in vivo expression functionality the construct.

The term "subject" as used herein refers to any species of the animal kingdom. In preferred embodiments it refers more specifically to humans and animals used for: pets (e.g. cats, dogs, etc.); work (e.g. horses, cows, etc.); food (chicken, fish, lambs, pigs, etc); and all others known in the art.

The term "promoter" as used herein refers to a sequence of DNA that directs the transcription of a gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "coding region" as used herein refers to any portion of the DNA sequence that is transcribed into messenger RNA (mRNA) and then translated into a sequence of amino acids characteristic of a specific polypeptide.

The term "analog" as used herein includes any mutant of GHRH, or synthetic or naturally occurring peptide fragments of GHRH, such as HV-GHRH (SEQID#1), TI-GHRH (SEQID#2), TV-GHRH (SEQID#3), 15/27/28-GHRH (SEQID#4), (1-44)NH$_2$ (SEQID#5) or (1-40)OH (SEQID#6) forms, or any shorter form to no less than (1-29) amino acids.

The term "delivery" as used herein is defined as a means of introducing a material into a subject, a cell or any recipient, by means of chemical or biological process, injection, mixing, electroporation, sonoporation, or combination thereof, either under or without pressure.

The term "growth hormone" ("GH") as used herein is defined as a hormone that relates to growth and acts as a chemical messenger to exert its action on a target cell.

The term "growth hormone releasing hormone" ("GHRH") as used herein is defined as a hormone that facilitates or stimulates release of growth hormone, and in a lesser extent other pituitary hormones, as prolactin.

The term "regulator protein" as used herein refers protein that increasing the rate of transcription in response to an inducing agent.

The term "modified cells" as used herein is defined as the cells from a subject that have an additional nucleic acid sequence introduced into the cell.

The term "lean body mass" ("LBM") as used herein is defined as the mass of the body of an animal attributed to non-fat tissue such as muscle.

The term "cassette" as used herein is defined as one or more transgene expression vectors.

The term "post-injection" as used herein refers to a time period following the introduction of a nucleic acid cassette that contains heterologous nucleic acid sequence encoding GHRH or biological equivalent thereof into the cells of the subject and allowing expression of the encoded gene to occur while the modified cells are within the living organism.

The term "heterologous nucleic acid sequence" as used herein is defined as a DNA sequence consisting of differing regulatory and expression elements.

The term "regulator protein" as used herein refers to any protein that can be used to control the expression of a gene.

The term "electroporation" as used herein refers to a method that utilized electric pulses to deliver a nucleic acid sequence into cells.

The term "poly-L-glutamate ("PLG")" as used herein refers to a biodegradable polymer of L-glutamic acid that is suitable for use as a vector or adjuvant for DNA transfer into cells with or without electroporation.

In an embodiment of the present invention, a nucleic acid expression construct is utilized in a plasmid meditated gene supplementation method. The consequence of the claimed supplementation method results in change in the pituitary lineage, with increased number of lactotrophs and an increase in the prolactin levels in an offspring from a female subject. The female subject may be a mother, a female who has never been pregnant or given birth before, or a surrogate mother, such as impregnated by fetal transplantation. Modification of the pituitary gland lineage in the female subject's offspring is achieved by utilizing a nucleic acid expression construct that is delivered into the cells of a female subject prior to or during gestation of the offspring. Although the nucleic acid constructs comprise a variety of different configurations, a preferred embodiment describes the construct comprising a promoter, a nucleotide sequence, and a 3' untranslated region. The nucleic acid sequence may comprise a growth hormone releasing hormone ("GHRH") or biological equivalent thereof, with a myogenic promoter, and a specified 3' untranslated region. Further embodiments also include the use of modified nucleic acid sequences that encode GHRH analogs that have been engineered to be protease resistant, but retain the functional biological activity of the wild-type GHRH.

Following the delivery of the nucleic acid expression construct into the female subject, the process of electroporation can be utilized to facilitate the uptake of the construct into the cells of the female subject. Although electroporation is a preferred method to deliver the nucleic acid expression construct into the cells of the female subject, other approaches can be utilized for this purpose, and are disclosed herein. In a specific embodiment of the current invention, muscle cells are the preferred cell type for delivery of the nucleic acid expression construct, however, other cell types (e.g. somatic cells, stem cells, or germ cells) can be utilized.

In order to assess growth effects of the growth hormone releasing hormone ("GHRH") utilizing plasmid meditated gene supplementation, several experiments that utilized myogenic vectors with an encoded GHRH gene were conducted. The outcome resulted in a co-pending patent application (i.e. U.S. patent application Ser. No. 10/021,403 filed on Dec. 12, 2001, and is hereby incorporated by reference) that disclosed methods used to treat pregnant sows in the last trimester of gestation with a vector containing a nucleic acid sequences for GHRH or biological equivalents thereof. Injection of the nucleic acid expression construct was followed by electroporation. Non-injected/electroporated sows were used as controls. The piglets from the GHRH injected sow were found to be bigger at birth. Cross-fostering studies were then performed, and at weaning, the piglets from injected sows remained bigger than controls. Cross-foster controls suckled on injected sows were also significantly bigger than their littermates. Multiple biochemical measurements were performed on the piglets and indicated that piglets born to sows treated with plasmid meditated gene supplementation of GHRH showed an increase in growth pattern over normal levels. Although not wanting to be bound by theory, this proof of principal experiment demonstrated that plasmid meditated gene supplementation could be useful to enhance certain animal characteristics throughout generations, while avoiding secondary effects linked with classical supplementation treatments.

Although not wanting to be bound by theory, pituitary gland development, including regulation and differentiation of somatotrophs depends upon paracrine processes within the pituitary itself and involves several growth factors and neuropeptides, such as vasoactive intestinal peptide, angiotensin, endothelin, and activin. Secretion of growth hormone ("GH") is stimulated by a natural GH secretagogue called growth hormone releasing hormone ("GHRH"), and inhibited by somatostatin ("SS"), which are both hypothalamic hormones. In healthy adult mammals, GH is released in a highly regulated, distinctive pulsatile pattern, which occurs when the stimulatory properties of GHRH are enabled by the diminution or withdrawal of SS secretion. The episodic pattern of GH secretion has profound importance for its biological activity and is required for the induction of its physiological effects at the peripheral level. Regulated GH secretion is essential for optimal linear growth, homeostasis of carbohydrate, protein, and fat metabolism, and for promoting a positive nitrogen balance (*Murray*, et al, 2000). These effects are mediated largely by its down-stream effector, insulin-like growth factor I ("IGF-I"). GH secretion also is influenced in vivo by ghrelin, the newly identified endogenous peptide ligand of the growth hormone secretagogue receptor, and is dependent on GHRH (*Hataya*, et al., 2001) for its GH-secretory activity (*Horvath*, et.al., 2001). In this invention, we disclose a method to alter pituitary gland development in the offspring of female subjects that were treated with plasmid mediated gene supplementation of GHRH. This method allows the pregnant subjects to be treated during the last trimester of gestation and alter the lineage specification of the pituitary gland as well as expression levels of growth hormone ("GH") and prolactin somatotrophs, without directly treating the offspring.

Hypothalamic tissue-specific expression of the GHRH gene is not required for its biological activity, as indicated by the biological activity of extra-cranially secreted GHRH (*Faglia*, et. al., 1992; *Melmed*, et.al., 1991). Recently, we showed that in pigs, ectopic expression of a novel, serum protease-resistant porcine GHRH driven by a synthetic muscle-specific promoter could elicit robust GH and IGF-I responses following its in vivo administration by intramuscular injection and electroporation (*Lopez-Calderon*, et. al., 1999). In the rat model, GHRH administration is effective in inducing pituitary GH mRNA expression and increasing GH content, as well as somatic growth, with the endogenous episodic GHRH secretory pattern present in males enhancing somatic growth over females (*Borski*, et.al., 2000). Although, the intergenerational effects on the offspring of pregnant animals with sustained GHRH expression are yet unknown, studies in adult animals indicate a potential plasticity of the GH somatotrophs in response to GHRH. Pathological GHRH stimulation (irrespective of its source, from transgenic models to pancreatic tumors) of GH secretion can result in proliferation, hyperplasia, and adenomas of the adenohypophysial cells (*Asa*, et. al., 1992; *Sano*, et.al., 1988). A preferred embodiment of the present invention utilizes the growth hormone-releasing hormone analog having a similar amino acid sequence of the wild-type ("wt") plasmid. As used herein, the term wt or "wild-type" can be the endogenous form of GHRH of any animal, or it may be a slightly modified form of the hormone, such as the porcine GHRH. A skilled artisan is aware that the endogenous GHRH has 44 amino acids, and an amide group at the end, with the correct notation for that form being (1-44)NH$_2$-GHRH. In a specific embodiment, a form with only 40 amino acids (lacking the last 4 amino acids) is used which also does not contain an amide group, and may be referred to as (1-40)OH-GHRH. This form as used herein may also be referred to as wild-type because it does not contain internal mutations if compared to the wild-type sequence, as opposed to other forms discussed herein (such as the HV-GHRH discussed below) having internal mutations introduced by site-directed mutagenesis. A skilled artisan is aware that the 1-40 form and shorter forms (for example, 1-32 or 1-29) exist naturally in humans and other mammals (even in different types of GHRH secreting tumors), and they have an activity comparable with the natural (1-44) NH$_2$. In a preferred embodiments of the present invention GHRH equivalents with increased stability over wild type GHRH peptides are utilized.

In other embodiments, different species of GHRH or an analog of GHRH are within the scope of the invention. In an object of the invention the residues encoded by the DNA are not modified post-translationally, given the nature of the nucleic acid administration.

The following species are within the scope of the present invention. U.S. Pat. No. 4,223,019 discloses pentapeptides having the amino acid sequence NH$_2$—Y—Z—E—G—JCOOH, wherein Y is selected from a group consisting of D-lysine and D-arginine; Z and J are independently selected from a group consisting of tyrosine, tryptophan, and phenylalanine; and E and G are independently selected from a group consisting of D-tyrosine, D-tryptophan, and D-phenylalanine. U.S. Pat. No. 4,223,020 discloses tetrapeptides having the following amino acid sequence NH$_2$—Y—Z—E—G—COOH wherein Y and G are independently selected from a group consisting of tyrosine, tryptophan, and phenylalanine; and Z and E are independently selected from a group consisting of D-tyrosine, D-tryptophan, and D-phenylalanine. U.S. Pat. No. 4,223,021 discloses pentapeptides having the following amino acid sequence NH$_2$—Y—Z—E—G—J—COOH wherein Y and G are independently selected from a group consisting of tyrosine, tryptophan, and phenylalanine; Z is selected from a group consisting of glycine, alanine, valine, leucine, isoleucine, proline, hydroxyproline, serine, threonine, cysteine, and methionine; and B and J are independently selected from a group consisting of D-tyrosine, D-tryptophan, and D-phenylalanine. U.S. Pat. No. 4,224,316 discloses novel pentapeptides having the following amino acid sequence NH$_2$—Y—Z—E—G—J—COOH wherein Y and E are independently selected from a group consisting of D-tyrosine, D-tryptophan, and D-phenylalanine; Z and G are independently selected from a group consisting of tyrosine, tryptophan, and phenylalanine; and J is selected from a group consisting of glycine, alanine, valine, leucine, isoleucine, proline, hydroxyproline, serine, threonine, cysteine, methionine, aspartic acid, glutamic acid, asparagine, glutamine, arginine, and lysine. U.S. Pat. No. 4,226,857 discloses pentapeptides having the following amino acid sequence NH$_2$—Y—Z—E—G—J—COOH wherein Y and G are independently selected from a group consisting of tyrosine, trytophan, and phenylalanine; Z and J are independently selected from a group consisting of D-tyrosine, D-tryptophan, and D-phenylalanine; and E is selected from a group consisting of glycine, alanine, valine, leucine, isoleucine, proline, hydroxyproline, serine, threonine, cysteine, methionine, aspartic acid, glutamic acid, asparagine, glutamine, and histidine. U.S. Pat. No. 4,228,155 discloses pentapeptides having the following amino acid sequence NH$_2$—Y—Z—E—G—J—COOH wherein Y is selected from a group consisting of tyrosine, D-tyrosine, tryptophan, D-tryptophan, phenylalanine, and D-phenylalanine; Z and B are independently selected from a group consisting of D-tyrosine, D-tryptophan, and D-phenylalanine; G is selected from a group consisting of lysine and arginine; and J is selected from a group consisting of glycine, alanine, valine, leucine, isoleucine, proline, hydroxyproline, serine, threonine, cysteine, and methionine. U.S. Pat. No. 4,228,156 discloses tripeptides having the following amino acid sequence NH$_2$—Y—Z—E—COOH wherein Y and Z are independently selected from a group consisting of D-tyrosine, D-tryptophan, and D-phenylalanine; and E is selected from a group consisting of tyrosine, tryptohan, and phenylalanine. U.S. Pat. No. 4,228,158 discloses pentapeptides having the following amino acid sequence NH2—Y—Z—E—G—J—COOH wherein Y and G are independently selected from a group consisting oftyrosine, tryptophan, and phenylalanine, Z and E are independently selected from a group consisting of D-tyrosine, D-tryptophan, and D-phenylalanine; and J is selected from a group consisting of natural amino acids and the D-configuration thereof. U.S. Pat. No. 4,833,166 discloses a synthetic peptide having the formula: H-Asp-Pro-Val-Asn-Ile-Arg-Ala-Phe-Asp-Asp-Val-Leu-Y (SEQID No. 16) wherein Y is OH or NH2 or a non-toxic salt thereof and A synthetic peptide having the formula: H-Val-Glu-Pro-Gly -Ser-Leu-Phe-Leu-Val-Pro-Leu-Pro-Leu-Leu-Pro-Val-His-Asp-Phe-Val-Gln-Gln-Phe-Ala-Gly-Ile-Y (SEQID No. 17) wherein Y is OH or NH$_2$ or a non-toxic salt thereof. Draghia-Akil, et al. (1997) utilize a 228-bp fragment of hGHRH which encodes a 31-amino-acid signal peptide and an entire mature peptide human GHRH (1-44)OH (Tyri Leu44).

The embodiments of the present invention include: (1) a method for changing the pituitary gland lineage, with an increased number of somatotrophs and lactotrophs in an offspring; and (2) a method for stimulating production of prolactin in an offspring at a level greater than that associated with normal growth. All of these methods include the step of introducing a nucleic acid construct or plasmid vector into the mother of the offspring during gestation of the offspring or during a previous pregnancy, wherein said vector comprises a promoter; a nucleotide sequence, such as one encoding a growth hormone releasing hormone or biological equivalent thereof; and a 3' untranslated region operatively linked sequentially at appropriate distances for functional expression.

It is an object of the present invention to change the pituitary lineage, and increase levels of prolactin in an animal, preferably an offspring from a mother. The preferred embodiments allow modifications in the pituitary lineage, and increase levels of prolactin in an animal for long terms, such as greater than a few weeks or greater than a few months. In a specific embodiment, this is achieved by administering growth hormone releasing hormone into the mother of the offspring, preferably in a nucleic acid form. In a preferred embodiment the GHRH nucleic acid is maintained as an episome in a muscle cell. In a specific embodiment the increase in GHRH affects the pituitary gland by increasing the number of growth hormone producing cells, and consequently changes their cellular lineage. Although not wanting to be bound by theory, the ratio of somatotrophs (growth hormone producing cells) is increased relative to other hormone producing cells in the pituitary, such as corticotrophs, lactotrophs, gonadotrophs, etc. Thus, the increase in growth hormone may be related to the rise in the number of growth hormone-producing cells. Likewise, increases in pituitary hormones, such as prolactin, may be related to the rise in the number of prolactin producing cells in the pituitary.

Prolactin is a single-chain protein hormone and is closely related to growth hormone. It is chiefly secreted by lactotrophs in the anterior pituitary. However, prolactin is also synthesized and secreted by a broad range of other cells in the body, most prominently various immune cells, the brain and the decidua of the pregnant uterus. Prolactin is also found in the serum of normal females and males. Prolactin secretion is pulsatile and also shows diurnal variation, with the serum concentration increasing during sleep and the lowest level occurs about 3 hours after waking. The secretion of prolactin is increased by stress and appears to be dependent upon a women's estrogen status.

The conventional view of prolactin is that the mammary gland is its major target organ, and stimulating mammary gland development along with milk production define its major functions. Although these views are true, such descriptions fail to convey an accurate depiction of this multifunctional hormone. For example, it is difficult to find a mammalian tissue that does not express prolactin receptors, and although the anterior pituitary is the major source of prolactin, the hormone is synthesized and secreted in many other tissues. Overall, several hundred different actions have been reported for prolactin in various species. Some of prolactin's major effects are summarized below.

Prolactin's major known functions are attributed with mammary gland development, milk production and reproduction. In the 1920's it was found that extracts of the pituitary gland, when injected into virgin rabbits, induced milk production. Subsequent research demonstrated that prolactin has two major roles in milk production: induction of lobuloalveolar growth of the mammary gland; and stimulation of lactogenesis after birth. Prolactin, along with cortisol and insulin, act together to stimulate transcription of the genes that encode milk proteins. Prolactin is also important in several non-lactational aspects of reproduction. For example, in some species (e.g. rodents, dogs, skunks), prolactin is necessary for maintenance of ovarian structures (i.e. corpora lutea) that secrete progesterone. Mice that are homozygous for an inactivated prolactin gene and thus incapable of secreting prolactin are infertile due to defects in ovulation, fertilization, preimplantation development and implantation. Prolactin also appears to have stimulatory effects in some species on reproductive or maternal behaviors such as nest building and retrieval of scattered young.

Prolactin also appears to elicit effects in the immune system. For example, the prolactin receptor is widely expressed by immune cells, and some types of lymphocytes synthesize and secrete prolactin. These observations suggest that prolactin may act as an autocrine or paracrine modulator of immune activity. Conversely, mice with homozygous deletions of the prolactin gene fail to show significant abnormalities in immune responses. A considerable amount of research is in progress to delineate the role of prolactin in normal and pathologic immune responses. Although the significance of these potential functions remains poorly understood, it is clear that prolactin can stimulate and enhance the immune system, which has been demonstrated in prior art (e.g. U.S. Pat. No. 5,605,885; and U.S. Pat. No. 5,872,127). Furthermore, the present invention indicates how increased prolactin levels are correlated with increased IGF-I levels.

In a preferred embodiment the promoter is a synthetic myogenic promoter and hGH 3' untranslated region (SEQID#8) is in the 3' untranslated region. However, the 3' untranslated region may be from any natural or synthetic gene. In a specific embodiment of the present invention there is utilized a synthetic promoter, termed SPc5-12 (SEQID#7) (*Li*, et al., 1999), which contains proximal serum response elements ("SRE") from skeletal α-actin, multiple MEF-2 sites, MEF-1 sites, and TEF-1 binding sites, and greatly exceeds the transcriptional potencies of natural myogenic promoters. In a preferred embodiment the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information (NCBI) GenBank database or the NCBI PubMed site. A skilled artisan is aware that these World Wide Web sites may be utilized to obtain sequences or relevant literature related to the present invention.

In a specific embodiment the human growth hormone ("hGH") hGH 3' (SEQID#8) untranslated region or polyadenylation signal is utilized in a nucleic acid construct, such as a plasmid.

In specific embodiments the nucleic acid construct is selected from the group consisting of a plasmid, a viral vector, a liposome, or a cationic lipid. In further specific embodiments said vector is introduced into myogenic cells or muscle tissue. In a further specific embodiment said animal is a human, a pet animal, a work animal, or a food animal.

In addition to the specific embodiment of introducing the nucleic acid construct into the animal via a plasmid vector, delivery systems for transfection of nucleic acids into the animal or its cells known in the art may also be utilized. For example, other non-viral or viral methods may be utilized. A skilled artisan recognizes that a targeted system for non-viral forms of DNA or RNA requires four components: 1) the DNA or RNA of interest; 2) a moiety that recognizes and binds to a cell surface receptor or antigen; 3) a DNA binding moiety; and 4) a lytic moiety that enables the transport of the complex from the cell surface to the cytoplasm. Further, liposomes and cationic lipids can be used to deliver the therapeutic gene combinations to achieve the same effect. Potential viral vectors include expression vectors derived from viruses such as adenovirus, retrovirus, vaccinia virus, herpes virus, and bovine papilloma virus. In addition, episomal vectors may be employed. Other DNA vectors and transporter systems are known in the art.

Vectors. One skilled in the art recognizes that expression vectors derived from various bacterial plasmids, retroviruses, adenovirus, herpes or from vaccinia viruses may be used for delivery of nucleotide sequences to a targeted organ, tissue or cell population. Methods which are well known to those skilled in the art can be used to construct recombinant vectors that will express the gene encoding the growth hormone releasing hormone analog. Transient expression may last for a month or more with a non-replicating vector and even longer if appropriate replication elements are a part of the vector system, wherein the term "vector" is used to refer to a carrier nucleic acid molecule into which a nucleic acid sequence can be inserted for introduction into a cell where the vector can be replicated and the nucleic acid sequence can be expressed. The term vector can also be referred to as a nucleic acid construct. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector or nucleic acid expression construct containing a nucleic acid sequence coding for at least part of a gene product capable of being transcribed. In a specific embodiment the nucleic acid sequence encodes part or all of GHRH. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

In a preferred embodiment, the nucleic acid construction construct or vector of the present invention is a plasmid which comprises a synthetic myogenic (muscle-specific) promoter, a nucleotide sequence encoding a growth hormone releasing hormone or its analog, and a 3' untranslated region. In alternative embodiments, the vectors is a viral vector, such as an adeno-associated virus, an adenovirus, or a retrovirus. In alternative embodiments, skeletal alpha-actin promoter, myosin light chain promoter, cytomegalovirus promoter, or SV40 promoter can be used. In other alternative embodiments, human growth hormone, bovine growth hormone, SV40, or skeletal alpha actin 3' untranslated regions are utilized in the vector.

Promoters and Enhancers. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one of naturally-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™. Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. In a specific embodiment the promoter is a synthetic myogenic promoter, such as is described in *Li*, et al. (1999).

The identity of tissue-specific promoters or elements, as well as assays to characterize their activity, is well known to those of skill in the art. Examples of such regions include the human LIMK2 gene, the somatostatin receptor 2 gene, murine epididymal retinoic acid-binding gene, human CD4, mouse alpha2 (XI) collagen, D1A dopamine receptor gene, insulin-like growth factor II, human platelet endothelial cell adhesion molecule-1.

Initiation Signals and Internal Ribosome Binding Sites. A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Multiple Cloning Sites. Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites. Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

Polyadenylation Signals. In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine or human growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication. In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers. In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, such as the antibiotic resistance gene on the plasmid constructs (such as ampicylin, gentamicin, tetracycline or chloramphenicol).

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Host Cells. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems. Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, and which can be bought, for example, under the name MAXBAC® 2.0 from INVITROGEN® and BAC-PACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Mutagenesis. Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Site-Directed Mutagenesis. Structure-guided site-specific mutagenesis represents a powerful tool for the dissection and engineering of protein-ligand interactions. The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement. Comprehensive information on the functional significance and information content of a given residue of protein can best be obtained by saturation mutagenesis in which all 19 amino acid substitutions are examined. The shortcoming of this approach is that the logistics of multi-residue saturation mutagenesis are daunting. Hundreds, and possibly even thousands, of site specific mutants must be studied. However, improved techniques make production and rapid screening of mutants much more straightforward.

Dosage and Formulation. The composition (active ingredients; herein, vectors comprising a promoter; a nucleotide sequence encoding growth hormone releasing hormone ("GHRH") and a 3' untranslated region operatively linked sequentially at appropriate distances for functional expression) of this invention can be formulated and administered to affect a variety of growth deficiency states by any means that produces contact of the active ingredient with the agent's site of action in the body of an animal. The composition of the present invention is defined as a vector containing a nucleotide sequence encoding the compound of the invention, which is an amino acid sequence analog herein described. Said composition is administered in sufficient quantity to generate a therapeutically effective amount of said compound. One skilled in the art recognizes that the terms "administered" and "introduced" can be used interchangeably. They can be administered by any conventional means available for use in conjunction with pharmaceuticals, either as individual therapeutic active ingredients or in a combination of therapeutic active ingredients. In a preferred embodiment the active ingredient is administered alone or in a buffer such as PBS, but may be administered with a pharmaceutical carrier selected on the basis of the chosen route of administration and standard pharmaceutical practice. Such pharmaceutical compositions can be used for therapeutic or diagnostic purposes in clinical medicine, both human and veterinary. For example, they are useful in the treatment of growth-related disorders such as hypopituitary dwarfism resulting from abnormalities in growth hormone production. Furthermore they can also be used to stimulate the growth or enhance feed conversion efficiency of animals raised for meat production, to enhance milk production, and stimulate egg production.

The dosage administered comprises a therapeutically effective amount of active ingredient and will, of course, vary depending upon known factors such as the pharmacodynamic characteristics of the particular active ingredient and its mode and route of administration; type of animal; age of the recipient; sex of the recipient; reproductive status of the recipient; health of the recipient; weight of the recipient; nature and extent of symptoms; kind of concurrent treatment; frequency of treatment; and the effect desired. Appropriate dosages of the vectors of the invention to be administered will vary somewhat depending on the individual subject and other parameters. The skilled practitioner will be able to determine appropriate dosages based on the known circulating levels of growth hormone associated with normal growth and the growth hormone releasing activity of the vector. As is well known in the art, treatment of a female or mother to produce bigger animals will necessitate varying dosages from individual to individual depending upon the degree of levels of increase of growth hormone production required.

Thus, there is provided in accordance with this invention a method of increasing growth of an offspring which comprises administering to the female or mother of the offspring an amount of the analog of this invention sufficient to increase the production of growth hormone to levels greater than that which is associated with normal growth. Normal levels of growth hormone vary considerably among individuals and, for any given individual, levels of circulating growth hormone vary considerably during the course of a day.

Plasmid mediated gene supplementation and in vivo expression. Recently, the delivery of specific genes to somatic tissue in a manner that can correct inborn or acquired deficiencies and imbalances was proved to be possible. Gene-based drug delivery offers a number of advantages over the administration of recombinant proteins. These advantages include the conservation of native protein structure, improved biological activity, avoidance of systemic toxicities, and avoidance of infectious and toxic impurities. In addition, plasmid mediated gene supplementation allows for prolonged exposure to the protein in the therapeutic range, because the newly secreted protein is present continuously in the blood circulation.

Although not wanting to be bound by theory, the primary limitation of using recombinant protein is the limited availability of protein after each administration. Plasmid mediated gene supplementation using injectable DNA plasmid vectors overcomes this, because a single injection into the subject's skeletal muscle permits physiologic expression for extensive periods of time. Injection of the vectors can promote the production of enzymes and hormones in animals in a manner that more closely mimics the natural process. Furthermore, among the non-viral techniques for gene transfer in vivo, the direct injection of plasmid DNA into muscle tissue is simple, inexpensive, and safe.

In a plasmid based expression system, a non-viral gene vector may be composed of a synthetic gene delivery system in addition to the nucleic acid encoding a therapeutic gene product. In this way, the risks associated with the use of most viral vectors can be avoided. The non-viral expression vector products generally have low toxicity due to the use of "species-specific" components for gene delivery, which minimizes the risks of immunogenicity generally associated with viral vectors. Additionally, no integration of plasmid sequences into host chromosomes has been reported in vivo to date, so that this type of gene transfer should neither activate oncogenes nor inactivate tumor suppressor genes. As episomal systems residing outside the chromosomes, plasmids have defined pharmacokinetics and elimination profiles, leading to a finite duration of gene expression in target tissues.

Efforts have been made to enhance the delivery of plasmid DNA to cells by physical means including electroporation, sonoporation, and pressure. Injection by electroporation involves the application of a pulsed electric field to create transient pores in the cellular membrane without causing permanent damage to the cell, which allows for the introduction of exogenous molecules. By adjusting the electrical pulse generated by an electroporetic system, nucleic acid molecules can travel through passageways or pores in the cell that are created during the procedure. The electroporation technique has been used previously to transfect tumor cells after injection of plasmid DNA, or to deliver the antitumoral drug bleomycin to cutaneous and subcutaneous tumors. Electroporation also has been used in rodents and other small animals (Mir, et al., 1998; Muramatsu, et al., 1998). Advanced techniques of intramuscular injections of plasmid DNA followed by electroporation into skeletal muscle have been shown to lead to high levels of circulating growth hormone releasing hormone ("GHRH") (Draghia-Akli, et al, 1999).

The ability of electroporation to enhance plasmid uptake into the skeletal muscle has been well documented, as described above. In addition, plasmid formulated with poly-L-glutamate ("PLG") or polyvinylpyrolidone (PVP) has been observed to increase gene transfection and consequently expression to up to 10 fold into mice, rats and dog muscle. Although not wanting to be bound by theory, PLG will increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, which substantially increases the transfection efficiency.

The use of directly injectable DNA plasmid vectors has been limited in the past. The inefficient DNA uptake into muscle fibers after simple direct injection has led to relatively low expression levels, ant the duration of the transgene expression has been short. The most successful previous clinical applications have been confined to vaccines.

Although there are references in the art directed to electroporation of eukaryotic cells with linear DNA, these examples illustrate transfection into cell suspensions, cell cultures, and the like, and the transfected cells are not present in a somatic tissue.

Where appropriate, the plasmid mediated gene supplementation vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds.

Accordingly, the pharmaceutical composition of the present invention may be delivered via various routes and to various sites in an animal body to achieve a particular effect (see, e.g., *Rosenfeld* et al. (1991); *Rosenfeld* et al., (1991a); *Jaffe* et al., 1992). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is an object of the present invention that a single administration of a growth hormone releasing hormone is sufficient for multiple gestation periods and also provides a therapy that enhances the offspring's performances by enlarging the size of the pituitary gland and increasing the levels of prolactin.

The invention may be better understood with reference to the following examples, which are representative of some of the embodiments of the invention, and are not intended to limit the invention.

EXAMPLE 1

GHRH Super-active Analogs Increase GH Secretagogue Activity and Stability

GHRH has a relatively short half-life of about 12 minutes in the circulatory systems of both humans (*Frohman* et al., 1984) and pigs. By employing GHRH analogs that prolong its biological half-life and/or improve its GH secretagogue activity, enhanced GH secretion is achieved. Plasmid vectors containing the muscle specific synthetic promoter SPc5-12 (SEQID#7)were previously described (*Li*, et al., 1999). Wild type and mutated porcine GHRH cDNAs were generated by site directed mutagenesis of GHRH cDNA (SEQID#9) (Altered Sites II in vitro Mutagenesis System, Promega, Madison, Wis.), and cloned into the BamHI/Hind III sites of pSPc5-12, to generate pSP-wt-GHRH (SEQID#15), or pSP-HV-GHRH (SEQID#11), respectively. The 3' untranslated region (3'UTR) of growth hormone was cloned downstream of GHRH cDNA. The resultant plasmids contained mutated coding region for GHRH, and the resultant encoded amino acid sequences were not naturally present in mammals. Several different plasmids that encoded different mutated amino acid sequences of GHRH or functional biological equivalent thereof are as follows:

| Plasmid | Encoded Amino Acid Sequence | |
|---------|------------------------------|---|
| wt-GHRH | YADAIFTNSYRKVLGQLSARKLLQDIMSRQQGERNQEQGA-OH | (SEQID#10) |
| HV-GHRH | HVDAIFTNSYRKVLAQLSARKLLQDILNRQQGERNQEQGA-OH | (SEQID#11) |
| TI-GHRH | YIDAIFTNSYRKVLAQLSARKLLQDILNRQQGERNQEQGA-OH | (SEQID#12) |

-continued

| Plasmid | Encoded Amino Acid Sequence | |
|---|---|---|
| TV-GHRH | YVDAIFTNSYRKVLAQLSARKLLQDILNRQQGERNQEQGA-OH | (SEQID#13) |
| 15/27/28-GHRH | YADAIFTNSYRKVLAQLSARKLLQDILNRQQGERNQEQGA-OH | (SEQID#14) |

In general, the encoded GHRH or functional biological equivalent thereof is of formula:

—$X_1$—$X_2$—DAIFTNSYRKVL—$X_3$—QL-SARKLLQDI—$X_4$—$X_5$—RQQGERN-QEQGA—OH (SEQID#6)

wherein: $X_1$ is a D-or L-isomer of an amino acid selected from the group consisting of tyrosine ("Y"), or histidine ("H"); $X_2$ is a D-or L-isomer of an amino acid selected from the group consisting of alanine ("A"), valine ("V"), or isoleucine ("I"); $X_3$ is a D-or L-isomer of an amino acid selected from the group consisting of alanine ("A") or glycine ("G"); $X_4$ is a D-or L-isomer of an amino acid selected from the group consisting of methionine ("M"), or leucine ("L"); $X_5$ is a D-or L-isomer of an amino acid selected from the group consisting of serine ("S") or asparagines ("N").

Although not wanting to be bound by theory, the $X_3$ position contains a Gly15 that was substituted for Ala15 to increase α-helical conformation and amphiphilic structure to decrease cleavage by trypsin-like enzymes (Su et al., 1991). GHRH analogs with Ala15 substitutions display a 4-5 fold greater affinity for the GHRH receptor (Campbell et al., 1991). To reduce loss of biological activity due to oxidation of the Met, with slightly more stable forms using molecules with a free COOH-terminus (Kubiak et al., 1989), substitution of $X_4$ and $X_5$, Met27 and Ser28 for Leu27and Asn28 was performed. Thus, a triple amino acid substitution mutant denoted as GHRH-15/27/28 was formed. Dipeptidyl peptidase IV is the prime serum GHRH degradative enzyme (Walter et al., 1980; Martin et al., 1993). The $X_1$ and $X_2$ substitutions can be described as poorer dipeptidase substrates were created by taking GHRH15/27/28 and then by replacing Ile2 with Ala2 (GHRH-TI) or with Val2 (GHRH-TV), or by converting Tyr1 and Ala2 for His1 and Val2.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Functional biological equivalents are thus defined herein as those proteins (and polynucleotides) in selected amino acids (or codons) may be substituted. A peptide comprising a functional biological equivalent of GHRH is a polypeptide that has been engineered to contain distinct amino acid sequences while simultaneously having similar or improved biologically activity when compared to GHRH. For example one biological activity of GHRH is to facilitate growth hormone ("GH") secretion in the subject.

EXAMPLE 2

DNA Constructs

In a specific embodiment, a plasmid of pSPc5-12-HV-GHRH is utilized in the present invention. In another specific embodiment, a plasmid vector is utilized wherein the plasmid comprises a pVC0289 backbone; a promoter, such as of a GHRH cDNA, such as the porcine HV-GHRH (the mutated HV-GHRH cDNA); and a 3' untranslated region ("UTR"), such as from human growth hormone ("hGH").

To test the biological potency of the mutated porcine GHRH cDNA sequences, plasmid vectors were engineered that were capable of directing the highest level of skeletal muscle-specific gene expression by a synthetic muscle promoter, SPc5-12, which contains proximal serum response elements from skeletal α-actin (SREs), multiple MEF-2 sites, multiple MEF-1 sites, and TEF-1 binding sites (Li, et al., 1999). A 228-bp fragment of porcine GHRH, which encodes the 31 amino acid signal peptide and the entire mature peptide porcine GHRH (Tyr1-Gly40) and or the GHRH mutants, followed by the 3' untranslated region of human GH cDNA, were incorporated into myogenic GHRH expression vectors by methods well known in the art. The plasmid pSPc5-12 contains a 360 bp SacI/BamHI fragment of the SPc5-12 synthetic promoter (Li, et al., 1999) in the SacI/BamHI sites of pSK-GHRH backbone (Draghia-Akli et al., 1997).

The wild type and mutated porcine GHRH cDNAs were obtained by site directed mutagenesis of human GHRH cDNA utilizing the kit Altered Sites II in vitro Mutagenesis System (Promega; Madison, Wis.). The human GHRH cDNA was subcloned as a BamHI-Hind III fragment into the corresponding sites of the pALTER Promega vector and mutagenesis was performed according to the manufacturer's directions. The porcine wild type cDNA was obtained from the human cDNA by changing the human amino acids 34 and 38 using the primer of nucleic acid sequence: (5'-A-G-G-C-A-G-C-A-G-G-G-A-G-A-G-A-G-G-A-A-C-C-A-A-G-A-G-C-A-A-G-GA-G-C-A-T-A-A-T-G-A-C-T-G-C-A-G-3')(SEQID No. 18). The porcine HV mutations were made with the primer of nucleic acid sequence: (5'-A-C-C-C-T-C-A-G-G-A-T-G-C-G-G-C-G-G-C-A-C-G-T-A-G-A-T-G-C-C-A-T-C-T-T-C-A-C-C-A-A-C-3') (SEQ ID No. 19). The porcine 15Ala mutation was made with the primer of nucleic acid sequence: (5'-C-G-G-A-A-G-G-T-G-C-T-G-G-C-C-C-A-G-C-T-G-T-C-C-G-C-C-3 ')(SEQID No. 20). The porcine 27Leu28Asn mutation was made with the primer of nucleic acid sequence: (5'-C-T-G-C-T-C-C-A-G-G-A-C-A-T-C-C-T-G-A-A-C-A-G-G-C-A-G-C-A-G-G-G-A-G-A-G-3') (SEQ ID No. 21). Following mutagenesis the resulting clones were sequenced to confirm correctness and subsequently subcloned into the BamHII Hind III sites of pSK-GHRH described in this Example by methods well known to those in the art. Another plasmid that was utilized included the pSP-SEAP construct that contains the SacI/HindIII SPc5-12 fragment, SEAP gene and 5V40 3'UTR from pSEAP-2 Basic Vector (Clontech Laboratories, Inc., Palo Alto, Calif.). Plasmids were grown in E. coli DH5œ(Gibco BRL, Carlsbad, Calif.). Endotoxin-free plasmid (Qiagen Inc., Chatsworth, Calif., USA) preparations were diluted to 1 mg/ml in PBS, pH 7.4.

The plasmids described above do not contain polylinker, IGF-I gene, a skeletal alpha-actin promoter or a skeletal alpha actin 3' UTR/NCR. Furthermore, these plasmids were introduced by muscle injection, followed by in vivo electroporation, as described below.

EXAMPLE 3

Intramuscular Injection of Plasmid and Electroporation.

The nucleic acid constructs that were used in pregnant female rats are shown in FIG. 1. Timed-pregnant Wistar female rats were housed and cared for in the animal facility of Baylor College of Medicine, Houston, Tex. Animals were maintained under environmental conditions of 10 h light/14 h darkness, in accordance with NIH Guide, USDA and Animal Welfare Act guidelines, and the protocol was approved by the Institutional Animal Care and Use Committee. The experiment was repeated twice. On day 16 of gestation, dams (n=20/group) were weighed and anesthetized using a combination of 42.8 mg/ml ketamine, 8.2 mg/ml xylazine and 0.7 mg/ml acepromazine, administered i.m. at a dose of 0.5-0.7 ml/kg. The left tibialis anterior muscle was injected with 30 μg of pSP-HV-GHRH (SEQID#11) in 100 μl PBS using 0.3 cc insulin syringes (*Becton-Dickinson*, Franklin Lakes, N.J.). Control dams were injected with a similar construct driving the reporter, beta-galactosidase. For both groups, the injection was followed by caliper electroporation, as described previously (*Draghia-Akli*, et al. 1999). Briefly, two minutes after injection, the rat leg was placed between a two needles electrode, 1 cm in length, 26 gauge, 1 cm between needles (Genetronics, San Diego, Calif.) and electric pulses were applied. Three 60-ms pulses at a voltage of 100 V/cm were applied in one orientation, then the electric field was reversed, and three more pulses were applied in the opposite direction. The pulses were generated with a T-820 Electro Square Porator (Genetronics, San Diego, Calif.).

EXAMPLE 4

Increased Body Weight for Offspring of Injected Dams

All injected dams gave birth at 20-22 days of gestation. In the first study 240 offspring and in the second study 60 offspring were analyzed from two weeks of age to 5 months of age (2, 3, 6, 8, 12, 16, 24 weeks after birth). Body weights were recorded at these time points using the same calibrated balance. The average number of pups per litter was similar between groups (pregnant rats treated with GHRH ("I"), n=10.8±0.75 pups/litter; controls ("C") n=11.75±0.5 pups/litter). At birth litter size was adjusted to equalize the numbers of pups to 10 pups/dam.

Figure 2:
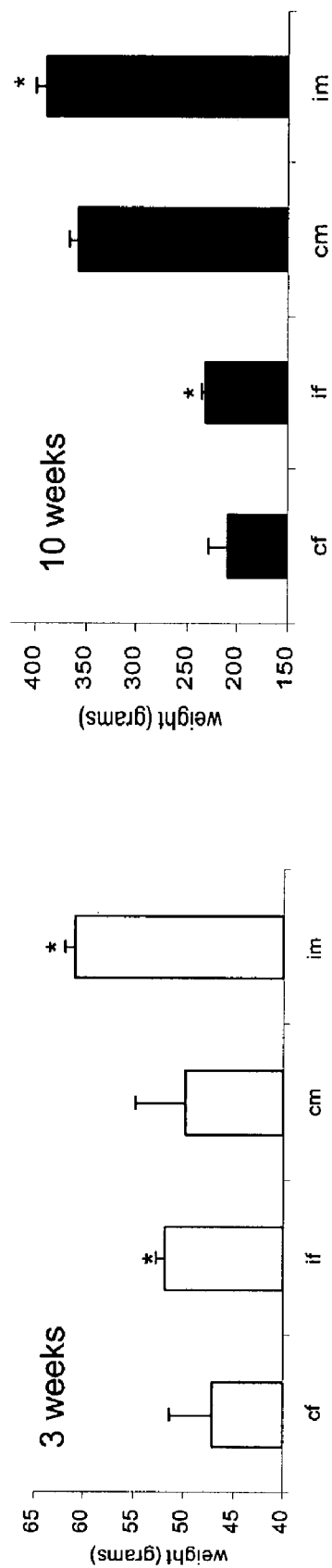
FIG. 2 shows the increased postnatal growth in offspring from rats treated with the nucleic acid constructs pSP-HV-GHRH (SEQID#11) and beta-galactosidase ("β-gal"). Significant weight differences (*) for both sexes were recorded at 3 weeks of age ($p<0.05$), and at 10 weeks of age ($p<0.05$). Female offspring from β-gal treated control dams ("CF"); female offspring of pSP-HV-GHRH (SEQID#11)-treated dams—("IF"), male offspring from β-gal treated control dams ("CM"); male offspring of pSP-HV-GHRH (SEQID#11)-treated dams—("IM")

At 2 weeks of age, the increased postnatal growth in offspring from dams treated with the nucleic acid constructs pSP-HV-GHRH (SEQID#11) ("I") and beta-galactosidase ("β-gal") ("C") were determined. Thus, at two weeks of age, the average pup weight was 9% greater for the offspring of I dams compared to C dams: I=31.47±0.52 g/pup vs. C=28.86±0.75 g/pup, p<0.014. At 3 weeks of age, were determined and shown in FIG. 2. Body weights for the female offspring of pSP-HV-GHRH (SEQID#11) treated dams ("IF") was significantly increased (i.e. 51.97±0.83 g) when compared to the control females offspring ("CF") (47.07±4.4 g, p<0.043). Male offspring from pSP-HV-GHRH (SEQID#11) treated dams ("IM") treated dams were 22% higher (i.e. 60.89±1.02 g) when compared to male offspring from control treated dams ("CM") (i.e. 49.85±4.9 g, p<0.001), as shown in FIG. 2. The weight difference was maintained up to 10 weeks of age. However, at 24 weeks of age, the weight differences between IM and CM was not significant. Significant weight differences (*) for both sexes were recorded at 3 weeks of age (p<0.05), and at 10 weeks of age (p<0.05). Female offspring from β-gal treated control dams ("CF"); female offspring of sp-HV-GHRH-treated dams—("IF"), male offspring from β-gal treated control dams ("CM"); male offspring of sp-HV-GHRH-treated dams—("IM").

The difference in weight between the progeny of treated and untreated dams was maintained to adulthood. Although not wanting to be bound by theory, this difference in weight was attributable largely to enhanced growth of the musculature, which in the female offspring was maintained for the entire period of the study (24 weeks). In male progeny, the higher muscle-to-body weight ratio was maintained only to puberty. This gender difference might be explained by differences in the hormonal profile of the two sexes. Males and females have similar amounts of testosterone until puberty, at which time testosterone levels increase much more dramatically in males (*Tipton*, et al., 2001). Although not wanting to be bound by theory, it is well-known that the postpubertal gonadal steroid environment plays an important role in determining anterior pituitary hormone synthesis and cellular composition. High testosterone levels present in post-puberal rodent may blunt the effect of increased GH production on the skeletal muscle. The rapid increase in muscle mass in the postnatal "growing phase" is due to growth of the muscle in both longitudinal and cross-sectional dimensions. The remaining increase in muscle mass in the "steady phase" (after the 10th week) is caused entirely by transverse growth, depending mainly on the muscle fiber hypertrophy (but may include increase of connective tissues) (*Tamaki*, et.al., 1995).

EXAMPLE 4

Increased Body/muscle Weight for Offspring of Injected Dams

At the end of the experiment animals were anesthetized, blood was collected by cardiac puncture, centrifuged immediately at 2° C., and stored at −80° C. prior to analysis. Organs (heart, liver, spleen, kidney, pituitary, brain, adrenals, skeletal muscles—tibialis anterior ("TA"), gastrocnemius ("G"), soleus ("S"), and extensor digitorum longus ("EDL")) from the offspring of treated and control dams were removed, weighed on an analytical balance and snap frozen in liquid nitrogen. The tibia was dissected and length was measured to the nearest 0.1 mm using calipers. Organ weight/total body weight was similar in between T and C at all time points after 3 weeks. At the first time point tested (3 weeks) the liver weight/total body weight (TM 0.042±0.0007 versus CM 0.035±0.002, p<0.0004, and TF 0.0404±0.0005 versus CF 0.0355±0.0008, p<0.0002) and the adrenal weight/total body weight (TM $4.4 \times 10^{-4} \pm 1.8 \times 10^{-5}$, versus CM $3.6 \times 10^{-4} \pm 1.7 \times 10^{-5}$, p<0.03, and TF $4.3 \times 10^{-4} \pm 0.9 \times 10^{-5}$, versus CF $3.2 \times 10^{-4} \pm 3.5 \times 10^{-5}$, p<0.0003) were increased in the offspring of the T dams. No differences in between organ weights/total body weights were noticed at subsequent time points analyzed. No associated pathology was observed in any of the animals through the entire period of the study.

Figure 3:
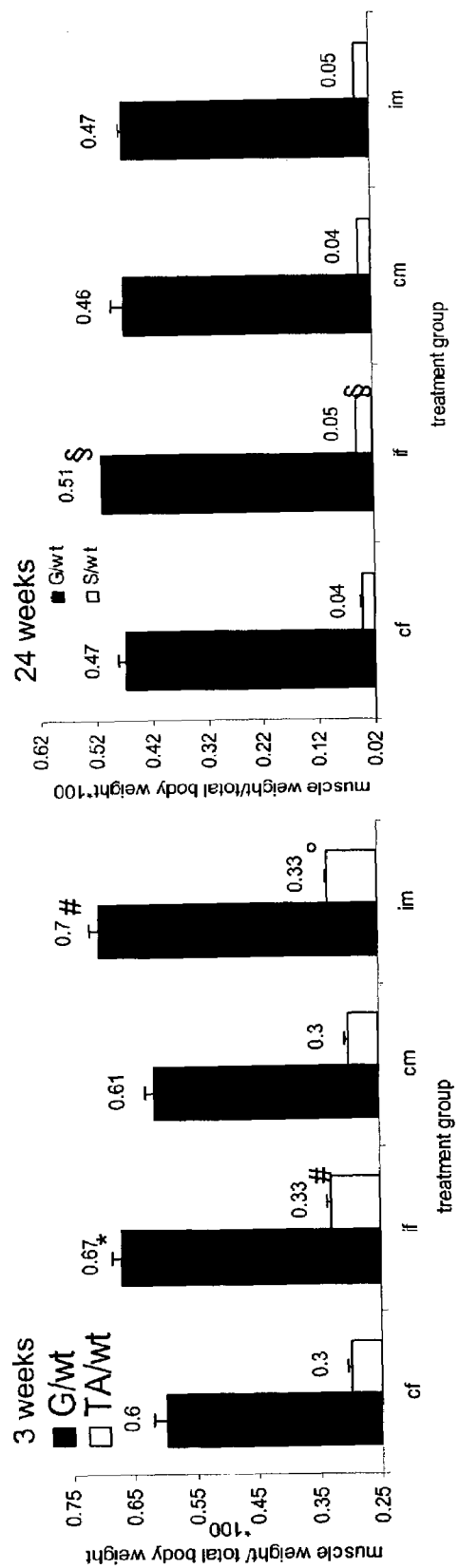
FIG. 3 shows muscle hypertrophy in the offspring of the pSP-HV-GHRH (SEQID#11) treated dams. Both male and female offspring from pSP-HV-GHRH (SEQID#11) treated animals had muscle hypertrophy at 3 weeks of age. Gastrocnemius weight/body weight ("G/wt"); Tibialis anterior weight/body weight ("TA/wt"), wherein the differences were significant at $*=p<0.02$; $\#=p<0.008$; $°=p<0.01$. At 24 weeks of age female offspring of the pSP-HV-GHRH (SEQID#11) treated dams maintained their muscle hypertrophy, whereas males were similar to controls. Gastrocnemius weight/total body weight ("G/wt"); and Soleus weight/total body weight ("S/wt") wherein the differences were significant at $\S=p<0.007$.

In contrast, both male and female offspring from pSP-HV-GHRH (SEQID#11) treated dams had muscle hypertrophy at 3 weeks of age with 10-12% differences in the gastrocnemius ("G") and tibialis anterior ("TA") muscle weights, even after the differences in body weights were adjusted. Gastrocnemius weight/body weight ("G/wt"); Tibialis anterior weight/body weight ("TA/wt"), wherein the differences were significant at * =p<0.02; #=p<0.008; °=p<0.01, as shown in FIG. 3. At 24 weeks of age the female offspring IF of the pSP-HV-GHRH (SEQID#11) treated dams maintained their muscle hypertrophy, whereas males IM were similar to controls.

EXAMPLE 5

Increased Serum IGF-I Levels for Offspring of Injected Dams

Figure 4:
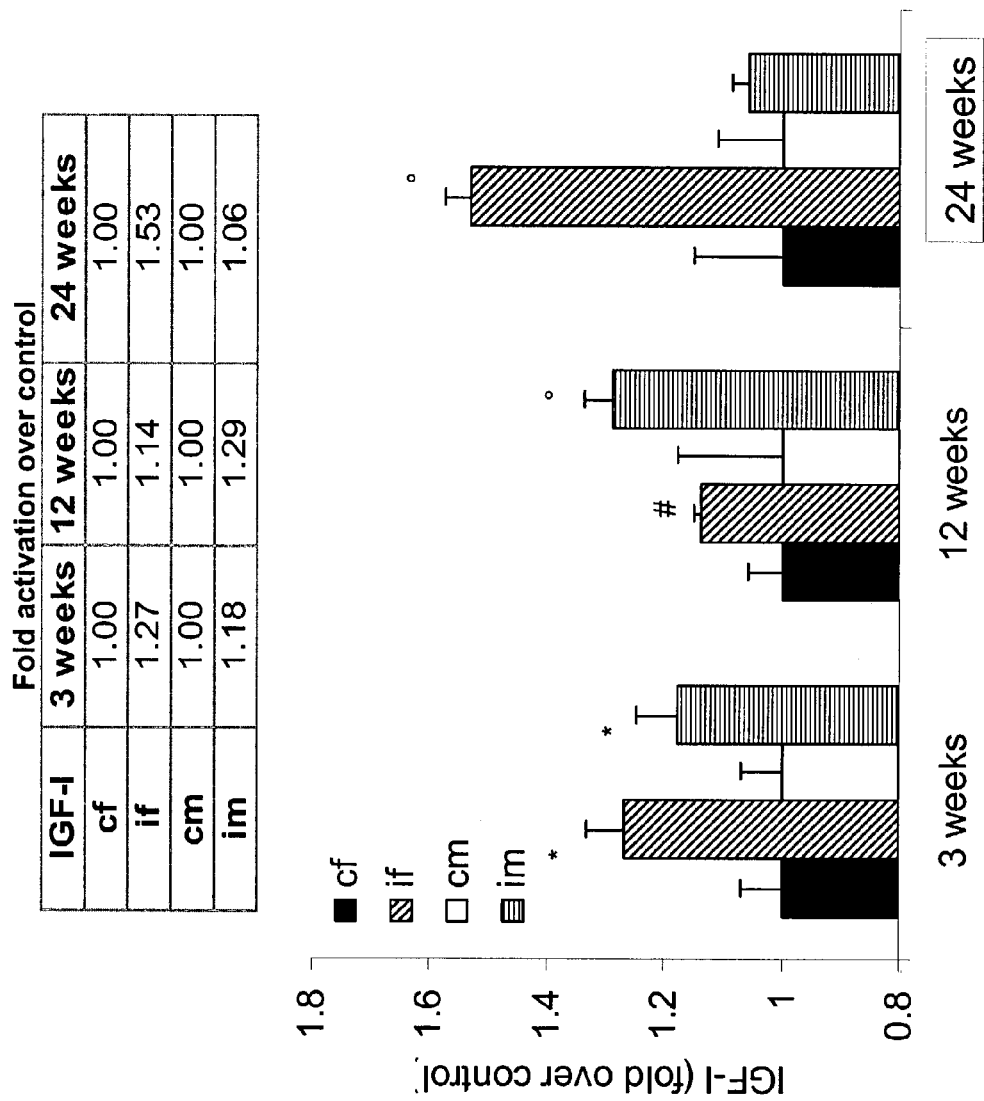
FIG. 4 shows the table and histogram of the fold activation of IGF-I levels in offspring from pSP-HV-GHRH (SEQID#11)-treated dams over the fold activation of the offspring from β-gal treated dams at 3, 12, and 24, weeks of age of the offspring. The circulating IGF-I levels were measured by specific rat radioimmunoassay ("RIA"). The histogram depicts fold IGF-I between age and sex matched controls, wherein the values are significant (*) at $p<0.05$. Female offspring from β-gal treated control dams ("CF"); female offspring of sp-HV-GHRH-treated dams—("IF"), male offspring from β-gal treated control dams ("CM"); male offspring of sp-HV-GHRH-treated dams—("IM"). Rat IGF-I was measured by specific radioimmunoassay (Diagnostic System Laboratories, Webster, Tex.). The sensitivity of the assay was 0.8 ng/ml; intra-assay and inter-assay coefficients of variation were 2.4% and 4.1%, respectively.

An indication of increased systemic levels of GHRH and GH is an increase in serum IGF-I concentration. Serum rat IGF-I was significantly higher in offspring of T dams compared to those from C dams at all time points tested until 24 weeks. FIG. 4 shows the table and histogram of the fold activation of IGF-I levels in offspring from sp-HV-GHRH-treated dams over the fold activation of the offspring from β-gal treated dams at 3, 12, and 24, weeks of age of the offspring. The circulating IGF-I levels were measured by specific rat radioimmunoassay ("RIA"). The histogram depicts fold IGF-I between age and sex matched controls, wherein the values are significant (*) at p<0.05. Female offspring from β-gal treated control dams ("CF"); female offspring of sp-HV-GHRH-treated dams—("IF"), male offspring from β-gal treated control dams ("CM"); male offspring of sp-HV-GHRH-treated dams—("IM"). Although not wanting to be bound by theory, the normal mechanisms responsible for the increase in serum GH levels that occur during pregnancy include: an increase in GH gene expression in the pituitary, a decrease in somatostatin secretion from the hypothalamus, an increase in immunoreactive-IGF-I content in both the hypothalamus and in the pituitary, and a significant decrease in circulating IGF-I. This state of GH resistance with a higher GH/IGF-I ratio could be important in providing supplementary nutrients to the fetus during the latter part of gestation when fetal growth is most rapid (*Escalada* et al., 1997). Our therapy further stimulated the maternal GHRH axis, fact that may explain the increased weight of the offspring of the treated animals at two weeks of age. Although not wanting to be bound by theory, it is also postulated that a ghrelin gene expression in the pituitary is developmentally regulated, and its expression is increased following GHRH infusion; the pituitary ghrelin/GHS-R signaling system could modulate the regulation of GH secretion by GHRH (*Kamegai*, et.al., 2001). Although not wanting to be bound by theory, some other possible explanations include: increased placental transport of nutrients. Postnatal, the growth curve could also be changed by increased milk production in the dam. Milk and colostrums contain a variety of proteins, peptides and steroids that possess biological activity (*Grosvenor*, et.al., 1993), that can be absorbed in the early neonatal period (before the "gut closure") into serum as intact and/or low-molecular weight processed forms (*Gonnella*, et.al., 1989). It is known that is rats, the concentration of GHRH in milk exceeds that in plasma by several fold; in addition the neonatal rat pituitary exhibits a greater sensitivity to the stimulatory effects of GHRH (*Szabo*, et.al., 1986). Thus, milk GHRH may function transiently to stimulate pituitary differentiation of the offspring.

EXAMPLE 6

Increased Serum IGF-I Levels for Offspring of Injected Dams

Figure 5:
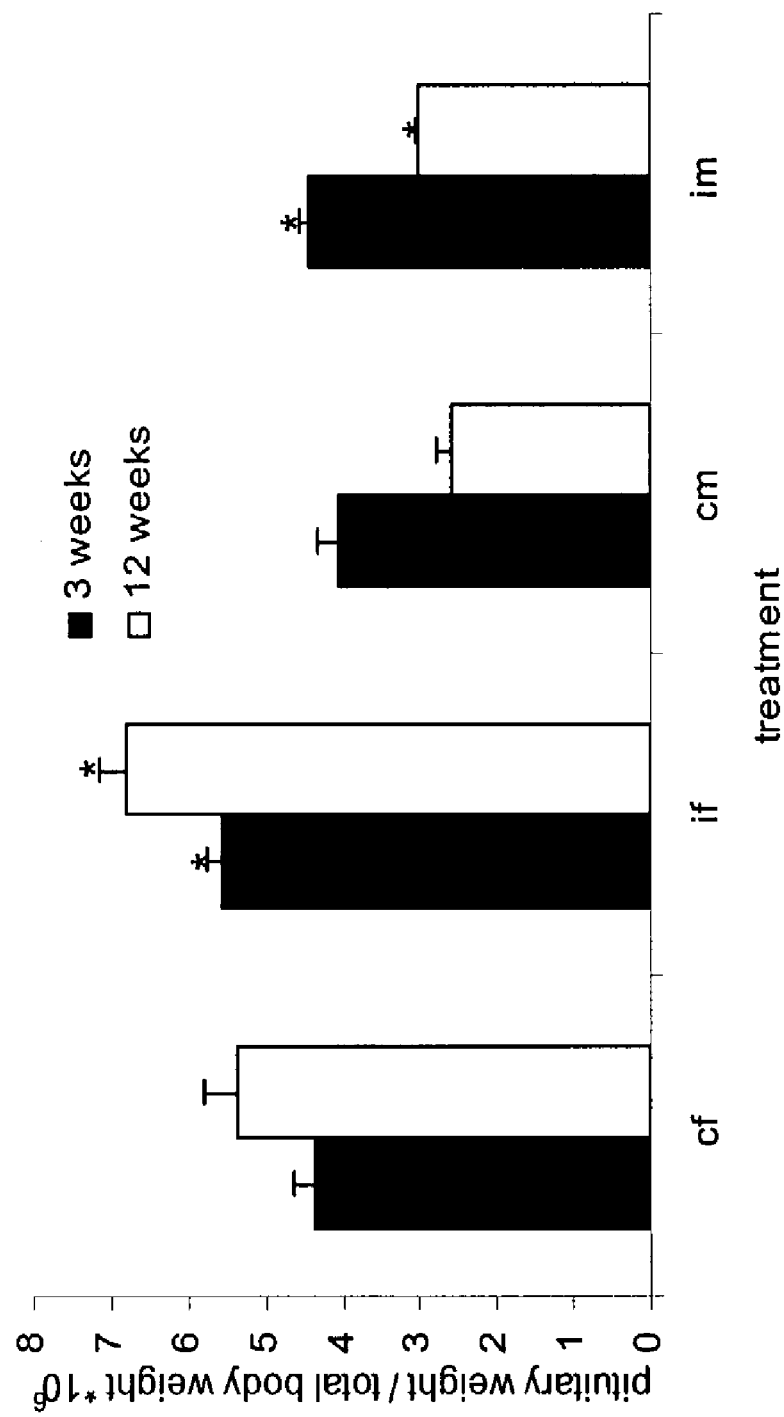
FIG. 5 shows that both male and female offspring from pSP-HV-GHRH (SEQID#11) treated dams had pituitary hypertrophy at 3 and 12 weeks, as measured by the pituitary weight/total body weight ratio.

As shown in FIG. 5, both male and female offspring from pSP-HV-GHRH (SEQID#11) treated dams had pituitary hypertrophy at 3 and 12 weeks. The pituitary glands were dissected and weighed within the first few minutes postmortem. Pituitary weight adjusted for body weight was significantly increased at least to 12 weeks of age; this difference was more prominent for IF. Although not wanting to be bound by theory, the increase in pituitary weight was probably due to hyperplasia of the somatotrophs and lactotrophs.

Figure 6:
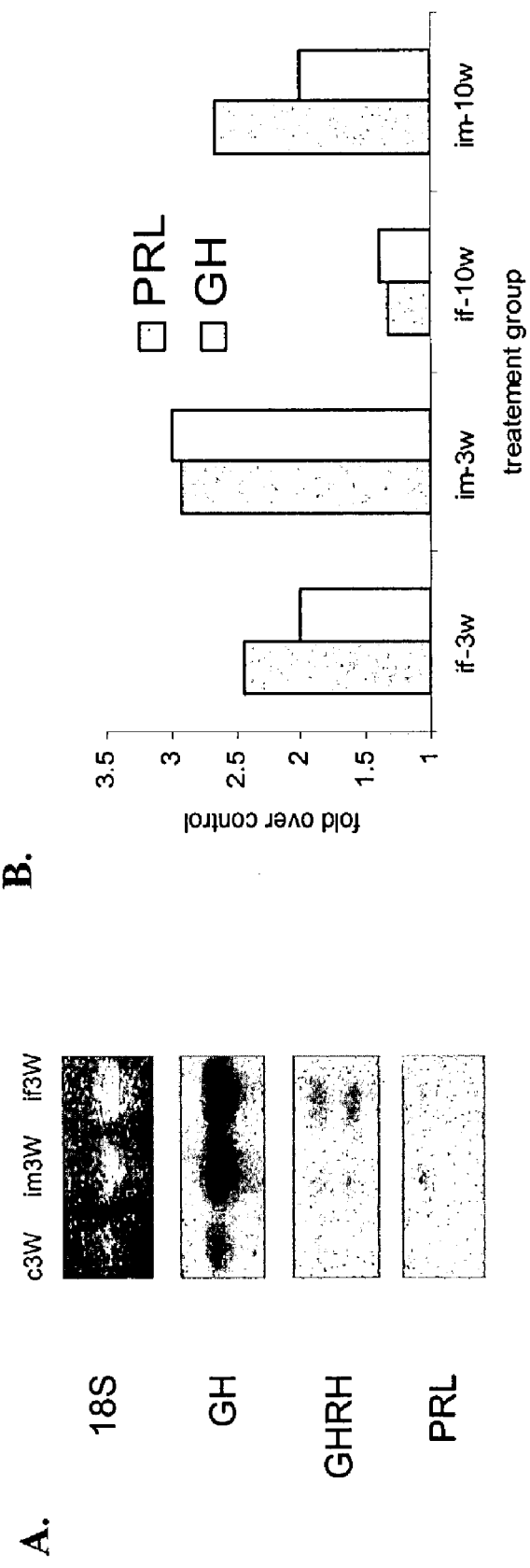
FIG. 6 shows a Northern blot analysis of pituitary tissue from male offspring ("c3W") from β-gal treated control dams and male ("IM3W") and female ("IF3W") offspring from pSP-HV-GHRH (SEQID#11) treated dams at 3 weeks (Panel A). RNA was visualized using probes for the 18s rRNA ("18S") loading marker; a rat growth hormone releasing hormone specific cDNA probe ("GHRH"); a growth hormone specific rat ("GH") cDNA probe; and a rat prolactin specific cDNA probe. The intensity of the bands was determined using a Phosphoimager (Molecular Dynamics) and associated software. Histogram (Panel B) shows fold increase in GH and PRL levels of the offspring from the pSP-HV-GHRH (SEQID#11) treated dams over the GH and PRL levels of the offspring from β-gal treated control dams. Pituitaries that had been snap frozen were homogenized. Total RNA was DNase I treated and 20 μg of RNA, DNA free was size separated in 1.5% agarose-formaldehyde gel and transferred to nylon membrane. The membranes were hybridized with specific GHRH, GH (gift from Dr. Kelly Mayo at Northwestern University, Chicago, Ill.) and PRL cDNA riboprobes $^{32}$P-labeled (gift from Dr. Kathleen Mahon at Baylor College of Medicine, Houston, Tex.).

The hypothesis that GHRH has a specific hypertrophic effect on GH and prolactin secreting cells is supported by the mRNA levels and immunohistochemical experimental evidence. For example, FIG. 6A shows a Northern blot analysis of pituitary tissue from male offspring ("c3W") from β-gal treated control dams and male ("IM3W") and female ("IF3W") offspring from pSP-HV-GHRH (SEQID#11) treated dams at 3 weeks. RNA was visualized using probes for the 18s rRNA ("18S") loading marker; a rat growth hormone releasing hormone specific cDNA probe ("GHRH"); a growth hormone specific rat ("GH") cDNA probe; and a rat prolactin specific cDNA probe. The intensity of the bands was determined using a Phosphoimager (Molecular Dynamics) and associated software. Histogram (6B) shows 2.5-fold increase in GH and PRL levels of the offspring from the pSP-HV-GHRH (SEQID#11) treated dams over the GH and PRL levels of the offspring from β-gal treated control dams. This difference in response was associated with a diminution of 20% in the endogenous rat GHRH mRNA levels.

Sections of pituitary glands were fixed immediately after dissection in 3% paraformaldehyde in PBS overnight. After fixation, samples were washed and stored in 70% ethanol until analyzed. Pituitary glands were paraffin embedded, and five micron-thick sections were cut, deparaffinized, and washed in PBS. Sections were blocked using a solution of 5% normal goat serum, 1% BSA, 0.05% Tween 20 in PBS for 1 hour at room temperature. The sections then were incubated for 2 hours at room temperature with the primary antibodies, rabbit-antirat-growth hormone (AFP5672099Rb, National Hormone and Peptide Program—NHPP) and rabbit-antirat-prolactin (AFP425-10-91 (NHPP)) diluted 1:2000 and 1:10000, respectively. After, washing off the primary antibodies, secondary peroxidase-coupled goat anti-rabbit IgG antibody (Sigma) at 1:5000 dilution was subsequently applied for 30 minutes at room temperature. Slides were washed in distilled water in between every step of the procedure. Peroxidase activity was revealed using a DAB substrate for 4 minutes (Vector laboratories, Burlingame, Calif.). Slides were counterstained with hematoxylin to visualize cell morphology and nuclei. Digital images of the slides were captured using a CoolSnap digital color camera (Roper Scientific, Tucson, Ariz.) with MetaMorph software (Universal Imaging Corporation, Downington, Pa.) and a Zeiss Axioplan 2 microscope with a (×40) objective (numerical aperture 0.75 plan).

Figure 7:
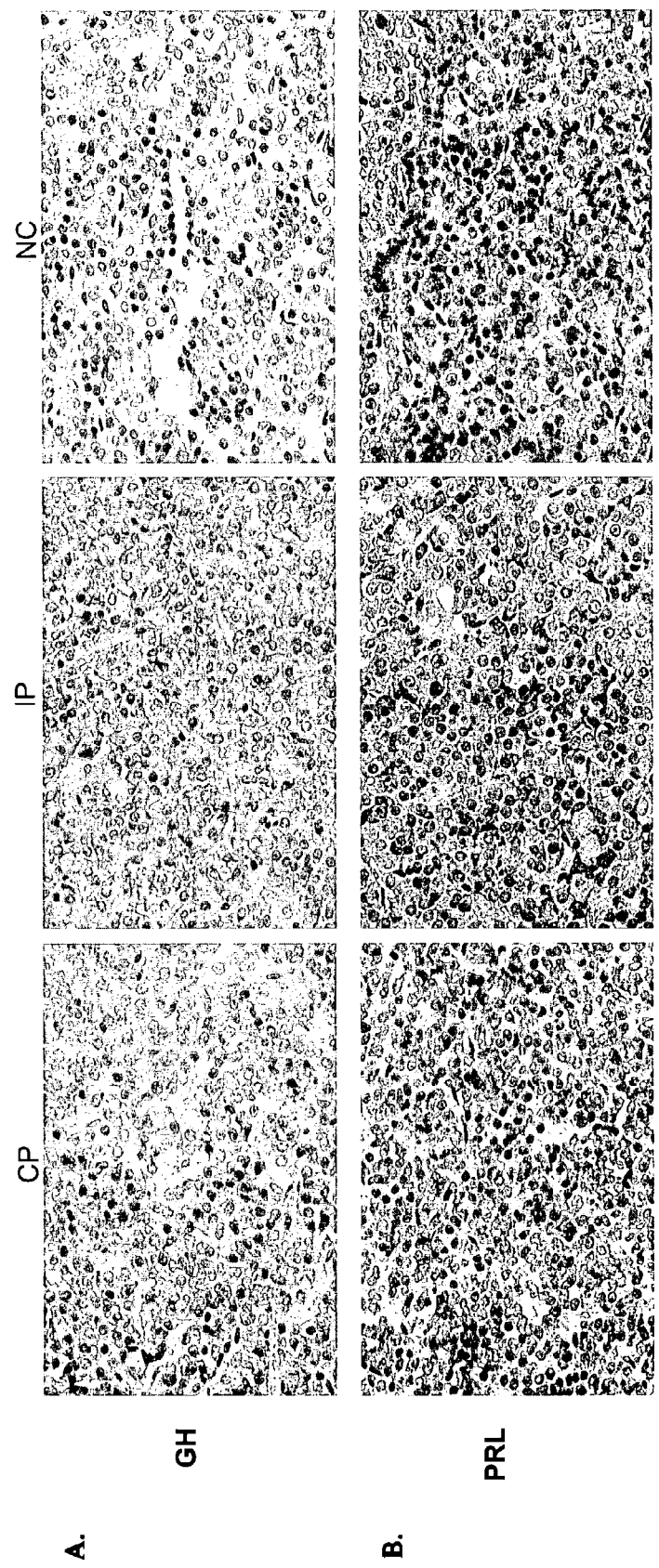
FIG. 7 shows immunostained sections of pituitary glands from the 3 week old offspring of pSP-HV-GHRH (SEQID#11) and β-gal treated dams. Panel A depicts rat GH-specific staining and Panel B depicts rat prolactin-specific staining, wherein the anterior pituitary from offspring of β-gal treated control dams ("CP"); anterior pituitary from offspring of pSP-HV-GHRH (SEQID#11) treated dams ("TP"); and the anterior pituitary from offspring of pSP-HV-GHRH (SEQID#11) treated dams with the immunostaining wherein no primary antibody was added to the incubation reaction ("NC"), are shown.

At the same age, pituitary sections immuno-stained with a rat GH-specific antibody (FIG. 7A), depicted an increased number of GH-immunoreactive cells (76% versus controls 39%), with an increased amount of GH per immunoreactive somatotroph. For each animal immunoreactive cells/total number of cells was counted in at least 5 fields and averaged.

Similarly, sections stained with a rat prolactin specific antibody (FIG. 7B), showed an increase in the number of prolactin-producing cells (25% versus 9% in controls).

In contrast to our results, previous studies conducted in GHRH transgenic animals observed a certain developmental pattern, with pituitary weight increasing mainly after the first 6 months of life, and with 70% of the glands contained grossly visible adenomas, that stained positively for GH, whereas only some showed scattered PRL staining. Although not wanting to be bound by theory, in our methods, rat dams were treated in the last trimester of gestation and pups pituitaries were most probably exposed to the hormone only a limited period of time, which determined a change in pituitary cell lineage, with somatotroph and lactotroph hyperplasia, without neoplastic changes within the pituitary.

In summary of the prior examples, enhanced animal growth occurred in offspring following a single electroporated injection of a plasmid expressing a mutated growth hormone releasing hormone (GHRH) cDNA, into the tibialis anterior muscles of pregnant female subjects. The newborn offspring from treated females were significantly bigger at birth. The longitudinal weight and body composition studies showed a difference in between the two sexes and with age. The offspring from treated females showed plasma IGF-I levels that were significantly elevated over offspring from control treated female subjects. The offspring from treated females from had larger pituitary glands, with apparent somatotroph hyperplasia and increased levels of pituitary derived hormones (e.g. GH and prolactin).

The use of recombinant GHRH, which is an upstream stimulator of GH, may be an alternate strategy to increase the size of the pituitary gland and prolactin levels in the offspring of treated mothers. However, the high cost of the recombinant peptides and the required frequency of administration currently limit the widespread use of such a recombinant treatment. These major drawbacks can be obviated by using a plasmid meditated gene supplementation method to direct the ectopic production of GHRH in pregnant females. Although not wanting to be bound by theory, similar treatments with recombinant GH or prolactin during the immediate postnatal period of the offspring will specifically increase pituitary size, increase prolactin levels, mitigate the deposition of body fat in later life, whilst enhancing lean tissue deposition, and enhancing the immune function.

By utilizing knowledge of specific pituitary/hypothalamic pathways and the functionality of extracranially secreted hormones, it is possible to treat many conditions utilizing a plasmid mediated introduction of a nucleic acid construct into a subject. Furthermore, it has been shown that some beneficial effects can be conferred to the offspring of female subjects that have been treated utilizing a plasmid mediated introduction of a nucleic acid construct, without treating the offspring directly. The consequence of the claimed supplementation method results is modification in the pituitary lineage, with an increased number of somatotrophs and lactotrophs and an increase in the prolactin levels in an offspring from the female subject. The female subject may be a mother, a female who has never been pregnant or given birth before, or a surrogate mother, such as impregnated by fetal transplantation. The benefit of this invention shows that offspring from animals that have been treated with a plasmid meditated gene supplementation method would benefit indirectly from the therapy without being individually treated. Such a method, would save a considerable amount financial resources for treating subjects, and if only mothers were treated, a reduction in the time for implementing such a therapy would also be expected.

One skilled in the art readily appreciates that the present invention is well adapted to carry out the objectives and obtain the ends and advantages mentioned as well as those inherent therein. Growth hormone, growth hormone releasing hormone, analogs, plasmids, vectors, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed:

1. A method of elevating prolactin levels in an offspring from a non-human female mammal comprising:
electroporating an effective amount of a nucleic acid expression construct into muscle cells of the non-human female mammal prior to or during gestation of the offspring, wherein the nucleic acid expression construct contains a nucleic acid sequence encoding a growth hormone releasing hormone ("GHRH") in the non-human female mammal during gestation; and wherein the vector comprises a promoter; a nucleotide sequence encoding the GHRH; and a 3' untranslated region, under conditions that promote expression of the nucleotide sequence, and wherein the introduction and expression of the nucleic acid expression construct results in elevating prolactin levels in said offspring.

2. The method of claim 1, further comprising selecting a promoter that comprises a synthetic myogenic promoter.

3. The method of claim 1, further comprising selecting the 3' untranslated region to comprise a human growth hormone ("hGH") 3' untranslated region (SEQ ID NO:8).

4. The method of claim 1, further comprising selecting the nucleic acid expression construct to be selected from group consisting of TI-GHRH plasmid (SEQ ID NO:12), TV-GHRH Plasmid (SEQ ID NO:13), 15/27/28 GHRH plasmid (SEQ ID NO:14), pSP-wt-GHRH plasmid (SEQ ID NO:15).

5. The method of claim 1, further comprising mixing the nucleic acid expression construct with a transfection-facilitating polypeptide.

6. The method of claim 5, further comprising selecting the transfection-facilitating polypeptide to comprise a charged polypeptide.

7. The method of claim 5, further comprising selecting the transfection-facilitating polypeptide to comprise poly-L-glutamate.

8. The method of claim 1, wherein the nucleic acid sequence encodes a growth-hormone-releasing-hormone ("GHRH"), and wherein the GHRH comprises an amino acid formula (SEQ ID NO:6):

-$X_1$-$X_2$-DAIFTNSYRKVL-$X_3$-QLSARKLLQDI-$X_4$-$X_5$-RQQGERNQEQGA-OH wherein the formula has the following characteristics:
$X_1$ is the amino acid tyrosine ("Y"), or histidine ("H");
$X_2$ is the amino acid alanine ("A"), valine ("V"), or isoleucine ("I");
$X_3$ is the amino acid alanine ("A") or glycine ("G");
$X_4$ is the amino acid methionine ("M"), or leucine ("L");
$X_5$ is the amino acid serine ("S") or asparagine ("N").

9. The method of claim 1, further comprising electroporating the nucleic acid expression construct into the non-human female mammal in multiple administrations.

10. The method of claim 1, further comprising selecting the third trimester of gestation of the offspring for electroporating the nucleic acid expression construct into cells of the non-human female mammal.

11. A method of elevating prolactin levels in an offspring from a non-human female mammal comprising:
electroporating an effective amount of a nucleic acid expression construct into muscle cells of the non-human female mammal prior to or during gestation of the offspring, wherein the nucleic acid expression construct comprises SEQ ID NO: 11 and wherein the introduction and expression of the nucleic acid expression construct results in elevating prolactin levels in said offspring.

12. The method of claim 11, further comprising mixing the nucleic acid expression construct with a transfection-facilitating polypeptide before electroporating.

13. The method of claim 12, further comprising selecting the transfection-facilitating polypeptide to comprise a charged polypeptide.

14. The method of claim 12, further comprising selecting the transfection-facilitating polypeptide to comprise poly-L-glutamate.

15. The method of claim 11, further comprising electroporating the nucleic acid expression construct into the non-human female mammal in multiple administrations.

16. The method of claim 11, further comprising selecting the third trimester of gestation of the offspring for electroporating the nucleic acid expression construct into cells of the non-human female mammal.

* * * * *

SEQUENCE LISTING

```
<160> NUMBER OF SEQ ID NOS: 15

<210> SEQ ID NO 1
<211> LENGTH: 40
<212> TYPE: PRT
<213> ORGANISM: artificial sequence
<220> FEATURE:
<223> OTHER INFORMATION: This is a growth hormone releasing hormone
      ("GHRH") analog.

<400> SEQUENCE: 1

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 2
<211> LENGTH: 40
<212> TYPE: PRT
```

```
<213> ORGANISM: artificial sequence
<220> FEATURE:
<223> OTHER INFORMATION: This is a growth hormone releasing hormone
      ("GHRH") analog.

<400> SEQUENCE: 2

Tyr Ile Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 3
<211> LENGTH: 40
<212> TYPE: PRT
<213> ORGANISM: artificial sequence
<220> FEATURE:
<223> OTHER INFORMATION: This is a growth hormone releasing hormone
      ("GHRH") analog.

<400> SEQUENCE: 3

Tyr Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 4
<211> LENGTH: 40
<212> TYPE: PRT
<213> ORGANISM: artificial sequence
<220> FEATURE:
<223> OTHER INFORMATION: This is a growth hormone releasing hormone
      ("GHRH") analog.

<400> SEQUENCE: 4

Tyr Ala Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 5
<211> LENGTH: 44
<212> TYPE: PRT
<213> ORGANISM: artificial sequence
<220> FEATURE:
<223> OTHER INFORMATION: This is a growth hormone releasing hormone
      ("GHRH") analog.

<400> SEQUENCE: 5

Thr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 6
<211> LENGTH: 40
```

```
<212> TYPE: PRT
<213> ORGANISM: artificial sequence
<220> FEATURE:
<223> OTHER INFORMATION: This is the artificial sequence for GHRH
      (1-40)OH.
<220> FEATURE:
<221> NAME/KEY: MISC_FEATURE
<222> LOCATION: (1)..(1)
<223> OTHER INFORMATION: Xaa at position 1 may be tyrosine, or histidine
<220> FEATURE:
<221> NAME/KEY: MISC_FEATURE
<222> LOCATION: (2)..(2)
<223> OTHER INFORMATION: Xaa at position 2 may be alanine, valine, or
      isoleucine.
<220> FEATURE:
<221> NAME/KEY: MISC_FEATURE
<222> LOCATION: (15)..(15)
<223> OTHER INFORMATION: Xaa at position 15 may be alanine, valine, or
      isoleucine.
<220> FEATURE:
<221> NAME/KEY: MISC_FEATURE
<222> LOCATION: (27)..(27)
<223> OTHER INFORMATION: Xaa at position 27 may be methionine, or
      leucine.
<220> FEATURE:
<221> NAME/KEY: MISC_FEATURE
<222> LOCATION: (28)..(28)
<223> OTHER INFORMATION: Xaa at position 28 may be serine or asparagine.

<400> SEQUENCE: 6

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Arg Asn Gln Glu Gln Gly Ala
        35                  40

<210> SEQ ID NO 7
<211> LENGTH: 323
<212> TYPE: DNA
<213> ORGANISM: artificial sequence
<220> FEATURE:
<223> OTHER INFORMATION: This is a nucleic acid sequence of a eukaryotic
      promoter c5-12.

<400> SEQUENCE: 7
cggccgtccg ccctcggcac catcctcacg acacccaaat atggcgacgg gtgaggaatg      60
gtggggagtt attttagag cggtgaggaa ggtgggcagg cagcaggtgt tggcgctcta     120
aaaataactc ccgggagtta ttttagagc ggaggaatgg tggacaccca aatatggcga    180
cggttcctca cccgtcgcca tatttgggtg tccgccctcg gccggggccg cattcctggg    240
ggccgggcgg tgctcccgcc cgcctcgata aaaggctccg gggccggcgg cggcccacga    300
gctacccgga ggagcgggag gcg                                            323

<210> SEQ ID NO 8
<211> LENGTH: 190
<212> TYPE: DNA
<213> ORGANISM: artificial sequence
<220> FEATURE:
<223> OTHER INFORMATION: Nucleic acid sequence of a human growth hormone
      poly A tail.

<400> SEQUENCE: 8
gggtggcatc cctgtgaccc ctccccagtg cctctcctgg ccctggaagt tgccactcca      60
gtgcccacca gccttgtcct aataaaatta agttgcatca ttttgtctga ctaggtgtcc    120
ttctataata ttatggggtg gagggggtg gtatggagca agggcaagt tgggaagaca      180
```

-continued

| | |
|---|---|
| acctgtaggg | 190 |

<210> SEQ ID NO 9
<211> LENGTH: 219
<212> TYPE: DNA
<213> ORGANISM: artificial sequence
<220> FEATURE:
<223> OTHER INFORMATION: cDNA for Porcine growth hormone releasing
      hormone.

<400> SEQUENCE: 9

| | |
|---|---|
| atggtgctct gggtgttctt ctttgtgatc ctcaccctca gcaacagctc ccactgctcc | 60 |
| ccacctcccc ctttgaccct caggatgcgg cggcacgtag atgccatctt caccaacagc | 120 |
| taccggaagg tgctggccca gctgtccgcc cgcaagctgc tccaggacat cctgaacagg | 180 |
| cagcagggag agaggaacca agagcaagga gcataatga | 219 |

<210> SEQ ID NO 10
<211> LENGTH: 40
<212> TYPE: PRT
<213> ORGANISM: artificial sequence
<220> FEATURE:
<223> OTHER INFORMATION: Amino acid sequence for porcine growth hormone
      releasing hormone.

<400> SEQUENCE: 10

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 11
<211> LENGTH: 3534
<212> TYPE: DNA
<213> ORGANISM: artificial sequence
<220> FEATURE:
<223> OTHER INFORMATION: Nucleic acid sequence of the HV-GHRH plasmid.

<400> SEQUENCE: 11

| | |
|---|---|
| gttgtaaaac gacggccagt gaattgtaat acgactcact atagggcgaa ttggagctcc | 60 |
| accgcggtgg cggccgtccg ccctcggcac catcctcacg acacccaaat atggcgacgg | 120 |
| gtgaggaatg gtggggagtt attttagag cggtgaggaa ggtgggcagg cagcaggtgt | 180 |
| tggcgctcta aaataactc ccgggagtta ttttagagc ggaggaatgg tggacaccca | 240 |
| aatatgcga cggttcctca cccgtcgcca tatttgggtg tccgccctcg gccggggccg | 300 |
| cattcctggg ggccgggcgg tgctcccgcc cgcctcgata aaggctccg ggccggcgg | 360 |
| cggcccacga gctacccgga ggagcgggag gcgccaagct ctagaactag tggatcccaa | 420 |
| ggcccaactc cccgaaccac tcagggtcct gtggacagct cacctagctg ccatggtgct | 480 |
| ctgggtgttc ttctttgtga tcctcaccct cagcaacagc tcccactgct ccccacctcc | 540 |
| cccttttgacc ctcaggatgc ggcggcacgt agatgccatc ttcaccaaca gctaccggaa | 600 |
| ggtgctggcc cagctgtccg cccgcaagct gctccaggac atcctgaaca ggcagcaggg | 660 |
| agagaggaac caagagcaag gagcataatg actgcaggaa ttcgatatca agcttatcgg | 720 |
| ggtggcatcc ctgtgacccc tccccagtgc ctctcctggc cctggaagtt gccactccag | 780 |
| tgcccaccag ccttgtccta ataaaattaa gttgcatcat tttgtctgac taggtgtcct | 840 |

```
tctataatat tatggggtgg aggggggtgg tatggagcaa ggggcaagtt gggaagacaa       900
cctgtagggc ctgcggggtc tattgggaac caagctggag tgcagtggca caatcttggc       960
tcactgcaat ctccgcctcc tgggttcaag cgattctcct gcctcagcct cccgagttgt      1020
tgggattcca ggcatgcatg accaggctca gctaattttt gttttttttgg tagagacggg     1080
gtttcaccat attggccagg ctggtctcca actcctaatc tcaggtgatc tacccacctt      1140
ggcctcccaa attgctggga ttacaggcgt gaaccactgc tcccttccct gtccttctga      1200
ttttaaaata actataccag caggaggacg tccagacaca gcataggcta cctggccatg      1260
cccaaccggt gggacatttg agttgcttgc ttggcactgt cctctcatgc gttgggtcca      1320
ctcagtagat gcctgttgaa ttcgataccg tcgacctcga ggggggcccc ggtaccagct      1380
tttgttccct ttagtgaggg ttaatttcga gcttggcgta atcatggtca tagctgtttc      1440
ctgtgtgaaa ttgttatccg ctcacaattc cacacaacat acgagccgga agcataaagt      1500
gtaaagcctg gggtgcctaa tgagtgagct aactcacatt aattgcgttg cgctcactgc      1560
ccgctttcca gtcgggaaac ctgtcgtgcc agctgcatta atgaatcggc caacgcgcgg      1620
ggagaggcgg tttgcgtatt gggcgctctt ccgcttcctc gctcactgac tcgctgcgct      1680
cggtcgttcg gctgcggcga gcggtatcag ctcactcaaa ggcggtaata cggttatcca      1740
cagaatcagg ggataacgca ggaaagaaca tgtgagcaaa aggccagcaa aaggccagga      1800
accgtaaaaa ggccgcgttg ctggcgtttt tccataggct ccgcccccct gacgagcatc      1860
acaaaaatcg acgctcaagt cagaggtggc gaaacccgac aggactataa agataccagg      1920
cgtttccccc tggaagctcc ctcgtgcgct ctcctgttcc gaccctgccg cttaccggat      1980
acctgtccgc ctttctccct tcgggaagcg tggcgctttc tcatagctca cgctgtaggt      2040
atctcagttc ggtgtaggtc gttcgctcca agctgggctg tgtgcacgaa ccccccgttc      2100
agcccgaccg ctgcgcctta tccggtaact atcgtcttga gtccaacccg gtaagacacg      2160
acttatcgcc actggcagca gccactggta acaggattag cagagcgagg tatgtaggcg      2220
gtgctacaga gttcttgaag tggtggccta actacggcta cactagaaga acagtatttg      2280
gtatctgcgc tctgctgaag ccagttacct tcggaaaaag agttggtagc tcttgatccg      2340
gcaaacaaac caccgctggt agcggtggtt tttttgtttg caagcagcag attacgcgca      2400
gaaaaaaagg atctcaagaa gatcctttga tcttttctac ggggtctgac gctcagaaga      2460
actcgtcaag aaggcgatag aaggcgatgc gctgcgaatc gggagcggcg ataccgtaaa      2520
gcacgaggaa gcggtcagcc cattcgccgc caagctcttc agcaatatca cgggtagcca      2580
acgctatgtc ctgatagcgg tccgccacac ccagccggcc acagtcgatg aatccagaaa      2640
agcggccatt ttccaccatg atattcggca agcaggcatc gccatgggtc acgacgagat      2700
cctcgccgtc gggcatgcgc gccttgagcc tggcgaacag ttcggctggc gcgagcccct      2760
gatgctcttc gtccagatca tcctgatcga caagaccggc ttccatccga gtacgtgctc      2820
gctcgatgcg atgtttcgct tggtggtcga atgggcaggt agccggatca gcgtatgca      2880
gccgccgcat tgcatcagcc atgatggata ctttctcggc aggagcaagg tgagatgaca      2940
ggagatcctg ccccggcact tcgcccaata gcagccagtc ccttcccgct tcagtgacaa      3000
cgtcgagcac agctgcgcaa ggaacgcccg tcgtggccag ccacgatagc cgcgctgcct      3060
cgtcctgcag ttcattcagg gcaccggaca ggtcggtctt gacaaaaaga accgggcgcc      3120
cctgcgctga cagccggaac acggcggcat cagagcagcc gattgtctgt tgtgcccagt      3180
```

-continued

```
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
gatgtgctgc aaggcgatta agttgggtaa cgccagggtt tcccagtca cgac          3534
```

<210> SEQ ID NO 12
<211> LENGTH: 3534
<212> TYPE: DNA
<213> ORGANISM: artificial sequence
<220> FEATURE:
<223> OTHER INFORMATION: Nucleic acid sequence of the TI-GHRH plasmid.

<400> SEQUENCE: 12

```
gttgtaaaac gacggccagt gaattgtaat acgactcact atagggcgaa ttggagctcc     60
accgcggtgg cggccgtccg ccctcggcac catcctcacg acacccaaat atggcgacgg    120
gtgaggaatg gtgggagtt attttagag cggtgaggaa ggtgggcagg cagcaggtgt    180
tggcgctcta aaataactc ccgggagtta tttttagagc ggaggaatgg tggacaccca    240
aatatggcga cggttcctca cccgtcgcca tatttgggtg tccgccctcg gccggggccg    300
cattcctggg ggccgggcgg tgctcccgcc cgcctcgata aaaggctccg gggccggcgg    360
cggcccacga gctacccgga ggagcgggag gcgccaagct ctagaactag tggatcccaa    420
ggcccaactc cccgaaccac tcagggtcct gtggacagct cacctagctg ccatggtgct    480
ctgggtgttc ttctttgtga tcctcacct cagcaacagc tcccactgct ccccacctcc    540
ccctttgacc ctcaggatgc ggcggtatat cgatgccatc ttcaccaaca gctaccggaa    600
ggtgctggcc cagctgtccg cccgcaagct gctccaggac atcctgaaca gcagcaggg    660 agagaggaac caagagcaag gagcataatg actgcaggaa ttcgatatca agcttatcgg    720
ggtggcatcc ctgtgacccc tcccagtgc ctctcctggc cctggaagtt gccactccag    780
tgcccaccag ccttgtccta ataaaattaa gttgcatcat tttgtctgac taggtgtcct    840
tctataatat tatgggggtgg aggggggtgg tatggagcaa ggggcaagtt gggaagacaa    900
cctgtagggc ctgcggggtc tattgggaac caagctggag tgcagtggca caatcttggc    960
tcactgcaat ctccgcctcc tgggttcaag cgattctcct gcctcagcct cccgagttgt   1020
tgggattcca ggcatgcatg accaggctca gctaattttt gttttttttgg tagagacggg   1080 gtttcaccat attggccagg ctggtctcca actcctaatc tcaggtgatc tacccacctt   1140
ggcctcccaa attgctggga ttacaggcgt gaaccactgc tcccttccct gtccttctga   1200 tttttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga ggggggggccc ggtaccagct   1380 tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
```

```
cagaatcagg ggataacgca ggaaagaaca tgtgagcaaa aggccagcaa aaggccagga      1800
accgtaaaaa ggccgcgttg ctggcgtttt tccataggct ccgcccccct gacgagcatc      1860
acaaaaatcg acgctcaagt cagaggtggc gaaacccgac aggactataa agataccagg      1920
cgtttccccc tggaagctcc ctcgtgcgct ctcctgttcc gaccctgccg cttaccggat      1980
acctgtccgc ctttctccct tcgggaagcg tggcgctttc tcatagctca cgctgtaggt      2040
atctcagttc ggtgtaggtc gttcgctcca agctgggctg tgtgcacgaa ccccccgttc      2100
agcccgaccg ctgcgcctta tccggtaact atcgtcttga gtccaacccg gtaagacacg      2160
acttatcgcc actggcagca gccactggta acaggattag cagagcgagg tatgtaggcg      2220
gtgctacaga gttcttgaag tggtggccta actacggcta cactagaaga acagtatttg      2280
gtatctgcgc tctgctgaag ccagttacct tcggaaaaag agttggtagc tcttgatccg      2340
gcaaacaaac caccgctggt agcggtggtt ttttgtttg caagcagcag attacgcgca      2400 gaaaaaagg atctcaagaa gatcctttga tcttttctac ggggtctgac gctcagaaga      2460
actcgtcaag aaggcgatag aaggcgatgc gctgcgaatc gggagcggcg ataccgtaaa      2520
gcacgaggaa gcggtcagcc cattcgccgc caagctcttc agcaatatca cgggtagcca      2580
acgctatgtc ctgatagcgg tccgccacac ccagccggcc acagtcgatg aatccagaaa      2640
agcggccatt ttccaccatg atattcggca agcaggcatc gccatgggtc acgacgagat      2700
cctcgccgtc gggcatgcgc gccttgagcc tggcgaacag ttcggctggc gcgagcccct      2760
gatgctcttc gtccagatca tcctgatcga caagaccggc ttccatccga gtacgtgctc      2820
gctcgatgcg atgtttcgct tggtggtcga atgggcaggt agccggatca agcgtatgca      2880
gccgccgcat tgcatcagcc atgatggata ctttctcggc aggagcaagg tgagatgaca      2940
ggagatcctg ccccggcact cgcccaata gcagccagtc ccttcccgct tcagtgacaa      3000
cgtcgagcac agctgcgcaa ggaacgcccg tcgtggccag ccacgatagc cgcgctgcct      3060
cgtcctgcag ttcattcagg gcaccggaca ggtcggtctt gacaaaaaga accgggcgcc      3120
cctgcgctga cagccggaac acggcggcat cagagcagcc gattgtctgt tgtgcccagt      3180
catagccgaa tagcctctcc acccaagcgg ccggagaacc tgcgtgcaat ccatcttgtt      3240
caatcatgcg aaacgatcct catcctgtct cttgatcaga tcttgatccc ctgcgccatc      3300
agatccttgg cggcaagaaa gccatccagt ttactttgca gggcttccca accttaccag      3360
agggcgcccc agctggcaat tccggttcgc ttgctgtcca taaaaccgcc cagtctagca      3420
actgttggga agggcgatcg gtgcgggcct cttcgctatt acgccagctg gcgaaagggg      3480
gatgtgctgc aaggcgatta agttgggtaa cgccagggtt ttcccagtca cgac           3534
```

<210> SEQ ID NO 13
<211> LENGTH: 3534
<212> TYPE: DNA
<213> ORGANISM: artificial sequence
<220> FEATURE:
<223> OTHER INFORMATION: Nucleic acid sequence of the TV-GHRH plasmid.

<400> SEQUENCE: 13

```
gttgtaaaac gacggccagt gaattgtaat acgactcact atagggcgaa ttggagctcc        60
accgcggtgg cggccgtccg ccctcggcac catcctcacg acacccaaat atggcgacgg       120
gtgaggaatg gtgggagtt atttttagag cggtgaggaa ggtgggcagg cagcaggtgt       180
tggcgctcta aaaataactc ccgggagtta ttttttagagc ggaggaatgg tggacaccca       240
```

-continued

| | |
|---|---|
| aatatggcga cggttcctca cccgtcgcca tatttgggtg tccgccctcg gccggggccg | 300 |
| cattcctggg ggccgggcgg tgctcccgcc cgcctcgata aaaggctccg gggccggcgg | 360 |
| cggcccacga gctacccgga ggagcgggag gcgccaagct ctagaactag tggatcccaa | 420 |
| ggcccaactc cccgaaccac tcagggtcct gtggacagtc cacctagctg ccatggtgct | 480 |
| ctgggtgttc ttctttgtga tcctcaccct cagcaacagc tcccactgct ccccacctcc | 540 |
| cccctttgacc ctcaggatgc ggcggtatgt agatgccatc ttcaccaaca gctaccggaa | 600 |
| ggtgctggcc cagctgtccg cccgcaagct gctccaggac atcctgaaca ggcagcaggg | 660 |
| agagaggaac caagagcaag gagcataatg actgcaggaa ttcgatatca agcttatcgg | 720 |
| ggtggcatcc ctgtgacccc tccccagtgc ctctcctggc cctggaagtt gccactccag | 780 |
| tgcccaccag ccttgtccta ataaaattaa gttgcatcat tttgtctgac taggtgtcct | 840 |
| tctataatat tatggggtgg aggggggtgg tatggagcaa ggggcaagtt gggaagacaa | 900 |
| cctgtagggc ctgcgggtc tattgggaac caagctggag tgcagtggca caatcttggc | 960 |
| tcactgcaat ctccgcctcc tgggttcaag cgattctcct gcctcagcct cccgagttgt | 1020 |
| tgggattcca ggcatgcatg accaggctca gctaattttt gttttttttgg tagagacggg | 1080 |
| gtttcaccat attggccagg ctggtctcca actcctaatc tcaggtgatc tacccacctt | 1140 |
| ggcctcccaa attgctggga ttacaggcgt gaaccactgc tcccttccct gtccttctga | 1200 |
| ttttaaaata actataccag caggaggacg tccagacaca gcataggcta cctggccatg | 1260 |
| cccaaccggt gggacatttg agttgcttgc ttggcactgt cctctcatgc gttgggtcca | 1320 |
| ctcagtagat gcctgttgaa ttcgataccg tcgacctcga gggggggccc ggtaccagct | 1380 |
| tttgttccct ttagtgaggg ttaatttcga gcttggcgta atcatggtca tagctgtttc | 1440 |
| ctgtgtgaaa ttgttatccg ctcacaattc cacacaacat acgagccgga agcataaagt | 1500 |
| gtaaagcctg gggtgcctaa tgagtgagct aactcacatt aattgcgttg cgctcactgc | 1560 |
| ccgctttcca gtcgggaaac ctgtcgtgcc agctgcatta atgaatcggc caacgcgcgg | 1620 |
| ggagaggcgg tttgcgtatt gggcgctctt ccgcttcctc gctcactgac tcgctgcgct | 1680 |
| cggtcgttcg gctgcggcga gcggtatcag ctcactcaaa ggcggtaata cggttatcca | 1740 |
| cagaatcagg ggataacgca ggaaagaaca tgtgagcaaa aggccagcaa aaggccagga | 1800 |
| accgtaaaaa ggccgcgttg ctggcgtttt tccataggct ccgcccccct gacgagcatc | 1860 |
| acaaaaatcg acgctcaagt cagaggtggc gaaacccgac aggactataa agataccagg | 1920 |
| cgtttccccc tggaagctcc ctcgtgcgct ctcctgttcc gaccctgccg cttaccggat | 1980 |
| acctgtccgc cttctccct tcgggaagcg tggcgctttc tcatagctca cgctgtaggt | 2040 |
| atctcagttc ggtgtaggtc gttcgctcca agctgggctg tgtgcacgaa ccccccgttc | 2100 |
| agcccgaccg ctgcgcctta tccggtaact atcgtcttga gtccaacccg gtaagacacg | 2160 |
| acttatcgcc actggcagca gccactggta acaggattag cagagcgagg tatgtaggcg | 2220 |
| gtgctacaga gttcttgaag tggtggccta actacggcta cactagaaga acagtatttg | 2280 |
| gtatctgcgc tctgctgaag ccagttacct tcggaaaaag agttggtagc tcttgatccg | 2340 |
| gcaaacaaac caccgctggt agcggtggtt ttttttgtttg caagcagcag attacgcgca | 2400 |
| gaaaaaaagg atctcaagaa gatcctttga tcttttctac ggggtctgac gctcagaaga | 2460 |
| actcgtcaag aaggcgatag aaggcgatgc gctgcgaatc gggagcggcg ataccgtaaa | 2520 |
| gcacgaggaa gcggtcagcc cattcgccgc caagctcttc agcaatatca cgggtagcca | 2580 |
| acgctatgtc ctgatagcgg tccgccacac ccagccggcc acagtcgatg aatccagaaa | 2640 |

```
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact cgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaccgcc cagtctagca    3420 actgttggga agggcgatcg gtgcgggcct cttcgctatt acgccagctg gcgaaagggg    3480
gatgtgctgc aaggcgatta agttgggtaa cgccagggtt ttcccagtca cgac          3534

<210> SEQ ID NO 14
<211> LENGTH: 3534
<212> TYPE: DNA
<213> ORGANISM: artificial sequence
<220> FEATURE:
<223> OTHER INFORMATION: Nucleic acid sequence of the 15/27/28 GHRH
      plasmid.

<400> SEQUENCE: 14
gttgtaaaac gacggccagt gaattgtaat acgactcact atagggcgaa ttggagctcc      60
accgcggtgg cggccgtccg ccctcggcac catcctcacg acacccaaat atggcgacgg     120
gtgaggaatg gtgggagtt attttagag cggtgaggaa ggtgggcagg cagcaggtgt      180
tggcgctcta aaataactc ccgggagtta tttttagagc ggaggaatgg tggacaccca     240
aatatggcga cggttcctca cccgtcgcca tatttgggtg tccgccctcg gccggggccg     300
cattcctggg ggccgggcgg tgctcccgcc cgcctcgata aaaggctccg gggccggcgg     360
cggcccacga gctacccgga ggagcgggag gcgccaagct ctagaactag tggatcccaa     420
ggcccaactc cccgaaccac tcagggtcct gtggacagct cacctagctg ccatggtgct     480
ctgggtgttc ttctttgtga tcctcacccct cagcaacagc tcccactgct ccccacctcc     540
ccctttgacc tcaggatgc ggcggtatat cgatgccatc ttcaccaaca gctaccggaa     600
ggtgctggcc cagctgtccg cccgcaagct gctccaggac atcctgaaca ggcagcaggg     660
agagaggaac caagagcaag gagcataatg actgcaggaa ttcgatatca agcttatcgg     720
ggtggcatcc ctgtgacccc tccccagtgc ctctcctggc cctggaagtt gccactccag     780
tgcccaccag ccttgtccta ataaaattaa gttgcatcat tttgtctgac taggtgtcct     840
tctataatat tatgggtgg aggggggtgg tatggagcaa gggcaagtt gggaagacaa     900 cctgtagggc ctgcggggtc tattgggaac caagctggag tgcagtggca caatcttggc     960
tcactgcaat ctccgcctcc tgggttcaag cgattctcct gcctcagcct cccgagttgt    1020
tgggattcca ggcatgcatg accaggctca gctaatttt gttttttggg tagagacggg    1080
gtttcaccat attggccagg ctggtctcca actcctaatc tcaggtgatc tacccacctt    1140
```

```
ggcctcccaa attgctggga ttacaggcgt gaaccactgc tcccttccct gtccttctga    1200
ttttaaaata actataccag caggaggacg tccagacaca gcataggcta cctggccatg    1260
cccaaccggt gggacatttg agttgcttgc ttggcactgt cctctcatgc gttgggtcca    1320
ctcagtagat gcctgttgaa ttcgataccg tcgacctcga ggggggccc ggtaccagct    1380 tttgttccct ttagtgaggg ttaatttcga gcttggcgta atcatggtca tagctgtttc    1440
ctgtgtgaaa ttgttatccg ctcacaattc cacacaacat acgagccgga agcataaagt    1500
gtaaagcctg gggtgcctaa tgagtgagct aactcacatt aattgcgttg cgctcactgc    1560
ccgctttcca gtcgggaaac ctgtcgtgcc agctgcatta atgaatcggc caacgcgcgg    1620
ggagaggcgg tttgcgtatt gggcgctctt ccgcttcctc gctcactgac tcgctgcgct    1680
cggtcgttcg gctgcggcga gcggtatcag ctcactcaaa ggcggtaata cggttatcca    1740
cagaatcagg ggataacgca ggaaagaaca tgtgagcaaa aggccagcaa aaggccagga    1800
accgtaaaaa ggccgcgttg ctggcgtttt tccataggct ccgcccccct gacgagcatc    1860
acaaaaatcg acgctcaagt cagaggtggc gaaacccgac aggactataa agataccagg    1920
cgtttccccc tggaagctcc ctcgtgcgct ctcctgttcc gaccctgccg cttaccggat    1980
acctgtccgc ctttctccct tcgggaagcg tggcgctttc tcatagctca cgctgtaggt    2040
atctcagttc ggtgtaggtc gttcgctcca agctgggctg tgtgcacgaa ccccccgttc    2100
agcccgaccg ctgcgcctta tccggtaact atcgtcttga gtccaacccg gtaagacacg    2160
acttatcgcc actggcagca gccactggta acaggattag cagagcgagg tatgtaggcg    2220
gtgctacaga gttcttgaag tggtggccta actacggcta cactagaaga acagtatttg    2280
gtatctgcgc tctgctgaag ccagttacct tcggaaaaag agttggtagc tcttgatccg    2340
gcaaacaaac caccgctggt agcggtggtt tttttgtttg caagcagcag attacgcgca    2400
gaaaaaaagg atctcaagaa gatcctttga tcttttctac ggggtctgac gctcagaaga    2460
actcgtcaag aaggcgatag aaggcgatgc gctgcgaatc gggagcggcg ataccgtaaa    2520
gcacgaggaa gcggtcagcc cattcgccgc caagctcttc agcaatatca cgggtagcca    2580
acgctatgtc ctgatagcgg tccgccacac ccagccggcc acagtcgatg aatccagaaa    2640
agcggccatt ttccaccatg atattcggca agcaggcatc gccatgggtc acgacgagat    2700
cctcgccgtc gggcatgcgc gccttgagcc tggcgaacag ttcggctggc gcgagcccct    2760
gatgctcttc gtccagatca tcctgatcga caagaccggc ttccatccga gtacgtgctc    2820
gctcgatgcg atgtttcgct tggtggtcga atgggcaggt agccggatca agcgtatgca    2880
gccgccgcat tgcatcagcc atgatggata ctttctcggc aggagcaagg tgagatgaca    2940
ggagatcctg ccccggcact tcgcccaata gcagccagtc ccttcccgct tcagtgacaa    3000
cgtcgagcac agctgcgcaa ggaacgcccg tcgtggccag ccacgatagc cgcgctgcct    3060
cgtcctgcag ttcattcagg gcaccggaca ggtcggtctt gacaaaaaga accgggcgcc    3120
cctgcgctga cagccggaac acggcggcat cagagcagcc gattgtctgt tgtgcccagt    3180
catagccgaa tagcctctcc acccaagcgg ccggagaacc tgcgtgcaat ccatcttgtt    3240
caatcatgcg aaacgatcct catcctgtct cttgatcaga tcttgatccc ctgcgccatc    3300
agatccttgg cggcaagaaa gccatccagt ttactttgca gggcttccca accttaccag    3360
agggcgcccc agctggcaat tccggttcgc ttgctgtcca taaaaccgcc cagtctagca    3420
actgttggga agggcgatcg gtgcgggcct cttcgctatt acgccagctg gcgaaagggg    3480
```

| | |
|---|---|
| gatgtgctgc aaggcgatta agttgggtaa cgccagggtt ttcccagtca cgac | 3534 |

<210> SEQ ID NO 15
<211> LENGTH: 3534
<212> TYPE: DNA
<213> ORGANISM: artificial sequence
<220> FEATURE:
<223> OTHER INFORMATION: This is the entire plasmid sequence for wildtype GHRH.

<400> SEQUENCE: 15

| | |
|---|---|
| gttgtaaaac gacggccagt gaattgtaat acgactcact atagggcgaa ttggagctcc | 60 |
| accgcggtgg cggccgtccg ccctcggcac catcctcacg acacccaaat atggcgacgg | 120 |
| gtgaggaatg gtggggagtt attttagag cggtgaggaa ggtgggcagg cagcaggtgt | 180 |
| tggcgctcta aaataactc ccgggagtta tttttagagc ggaggaatgg tggacaccca | 240 |
| aatatggcga cggttcctca cccgtcgcca tatttgggtg tccgccctcg gccggggccg | 300 |
| cattcctggg ggccgggcgg tgctcccgcc cgcctcgata aaaggctccg gggccggcgg | 360 |
| cggcccacga gctacccgga ggagcgggag gcgccaagct ctagaactag tggatcccaa | 420 |
| ggcccaactc cccgaaccac tcagggtcct gtggacagtc cacctagctg ccatggtgct | 480 |
| ctgggtgttc ttctttgtga tcctcaccct cagcaacagc tcccactgct ccccacctcc | 540 |
| ccctttgacc ctcaggatgc ggcggtatgc agatgccatc ttcaccaaca gctaccggaa | 600 |
| ggtgctggc cagctgtccg cccgcaagct gctccaggac atcatgagca ggcagcaggg | 660 |
| agagaggaac caagagcaag gagcataatg actgcaggaa ttcgatatca gcttatcgg | 720 |
| ggtggcatcc ctgtgacccc tccccagtgc ctctcctggc cctggaagtt gccactccag | 780 |
| tgcccaccag ccttgtccta ataaaattaa gttgcatcat tttgtctgac taggtgtcct | 840 |
| tctataatat tatggggtgg aggggggtgg tatggagcaa ggggcaagtt gggaagacaa | 900 |
| cctgtagggc ctgcggggtc tattgggaac caagctggag tgcagtggca caatcttggc | 960 |
| tcactgcaat ctccgcctcc tgggttcaag cgattctcct gcctcagcct cccgagttgt | 1020 |
| tgggattcca ggcatgcatg accaggctca gctaattttt gtttttttgg tagagacggg | 1080 |
| gtttcaccat attggccagg ctggtctcca actcctaatc tcaggtgatc tacccaccttt | 1140 |
| ggcctcccaa attgctggga ttacaggcgt gaaccactgc tcccttccct gtccttctga | 1200 |
| ttttaaaata actataccag caggaggacg tccagacaca gcataggcta cctggccatg | 1260 |
| cccaaccggt gggacatttg agttgcttgc ttggcactgt cctctcatgc gttgggtcca | 1320 |
| ctcagtagat gcctgttgaa ttcgataccg tcgacctcga gggggggccc ggtaccagct | 1380 |
| tttgttccct ttagtgaggg ttaatttcga gcttggcgta atcatggtca tagctgtttc | 1440 |
| ctgtgtgaaa ttgttatccg ctcacaattc cacacaacat acgagccgga agcataaagt | 1500 |
| gtaaagcctg gggtgcctaa tgagtgagct aactcacatt aattgcgttg cgctcactgc | 1560 |
| ccgctttcca gtcgggaaac ctgtcgtgcc agctgcatta atgaatcggc caacgcgcgg | 1620 |
| ggagaggcgg tttgcgtatt gggcgctctt ccgcttcctc gctcactgac tcgctgcgct | 1680 |
| cggtcgttcg gctgcggcga gcggtatcag ctcactcaaa ggcggtaata cggttatcca | 1740 |
| cagaatcagg ggataacgca ggaaagaaca tgtgagcaaa aggccagcaa aaggccagga | 1800 |
| accgtaaaaa ggccgcgttg ctggcgtttt tccataggct ccgccccct gacgagcatc | 1860 |
| acaaaaatcg acgctcaagt cagaggtggc gaaacccgac aggactataa agataccagg | 1920 |
| cgtttccccc tggaagctcc ctcgtgcgct ctcctgttcc gaccctgccg cttaccggat | 1980 |

-continued

```
acctgtccgc ctttctccct tcgggaagcg tggcgctttc tcatagctca cgctgtaggt      2040
atctcagttc ggtgtaggtc gttcgctcca agctgggctg tgtgcacgaa ccccccgttc      2100
agcccgaccg ctgcgcctta tccggtaact atcgtcttga gtccaacccg gtaagacacg      2160
acttatcgcc actggcagca gccactggta acaggattag cagagcgagg tatgtaggcg      2220
gtgctacaga gttcttgaag tggtggccta actacggcta cactagaaga acagtatttg      2280
gtatctgcgc tctgctgaag ccagttacct tcggaaaaag agttggtagc tcttgatccg      2340
gcaaacaaac caccgctggt agcggtggtt ttttttgtttg caagcagcag attacgcgca      2400
gaaaaaaagg atctcaagaa gatcctttga tcttttctac ggggtctgac gctcagaaga      2460
actcgtcaag aaggcgatag aaggcgatgc gctgcgaatc gggagcggcg ataccgtaaa      2520
gcacgaggaa gcggtcagcc cattcgccgc caagctcttc agcaatatca cgggtagcca      2580
acgctatgtc ctgatagcgg tccgccacac ccagccggcc acagtcgatg aatccagaaa      2640
agcggccatt ttccaccatg atattcggca agcaggcatc gccatgggtc acgacgagat      2700
cctcgccgtc gggcatgcgc gccttgagcc tggcgaacag ttcggctggc gcgagcccct      2760
gatgctcttc gtccagatca tcctgatcga caagaccggc ttccatccga gtacgtgctc      2820
gctcgatgcg atgtttcgct tggtggtcga atgggcaggt agccggatca agcgtatgca      2880
gccgccgcat tgcatcagcc atgatggata ctttctcggc aggagcaagg tgagatgaca      2940
ggagatcctg ccccggcact cgcccaata gcagccagtc ccttcccgct tcagtgacaa      3000
cgtcgagcac agctgcgcaa ggaacgcccg tcgtggccag ccacgatagc cgcgctgcct      3060
cgtcctgcag ttcattcagg gcaccggaca ggtcggtctt gacaaaaaga accgggcgcc      3120
cctgcgctga cagccggaac acggcggcat cagagcagcc gattgtctgt tgtgcccagt      3180
catagccgaa tagcctctcc acccaagcgg ccggagaacc tgcgtgcaat ccatcttgtt      3240
caatcatgcg aaacgatcct catcctgtct cttgatcaga tcttgatccc ctgcgccatc      3300
agatccttgg cggcaagaaa gccatccagt ttactttgca gggcttccca accttaccag      3360
agggcgcccc agctggcaat tccggttcgc ttgctgtcca taaaaccgcc cagtctagca      3420
actgttggga agggcgatcg gtgcgggcct cttcgctatt acgccagctg gcgaaagggg      3480
gatgtgctgc aaggcgatta agttgggtaa cgccagggtt ttcccagtca cgac           3534
```